US012570743B2

(12) United States Patent
Zhang et al.

(10) Patent No.: US 12,570,743 B2
(45) Date of Patent: Mar. 10, 2026

(54) BCMA-TARGETING ENGINEERED IMMUNE CELL AND USE THEREOF

(71) Applicant: GRACELL BIOSCIENCE (SHANGHAI) CO., LTD., Shanghai (CN)

(72) Inventors: Hua Zhang, Shanghai (CN); Lianjun Shen, Shanghai (CN); Huan Shi, Shanghai (CN); Wei Cao, Shanghai (CN); Chunhui Yang, Shanghai (CN); Liping Liu, Shanghai (CN)

(73) Assignee: GRACELL BIOSCIENCE (SHANGHAI) CO., LTD., Shanghai (CN)

( * ) Notice: Subject to any disclaimer, the term of this patent is extended or adjusted under 35 U.S.C. 154(b) by 1072 days.

(21) Appl. No.: 17/609,250

(22) PCT Filed: May 6, 2020

(86) PCT No.: PCT/CN2020/088835
§ 371 (c)(1),
(2) Date: Nov. 5, 2021

(87) PCT Pub. No.: WO2020/224605
PCT Pub. Date: Nov. 12, 2020

(65) Prior Publication Data
US 2022/0202864 A1 Jun. 30, 2022

(30) Foreign Application Priority Data
May 7, 2019 (CN) .......................... 201910376645.8

(51) Int. Cl.
| | |
|---|---|
| *A61K 35/17* | (2025.01) |
| *A61K 40/11* | (2025.01) |
| *A61K 40/31* | (2025.01) |
| *A61K 40/42* | (2025.01) |
| *A61P 35/00* | (2006.01) |
| *C07K 16/28* | (2006.01) |
| *C12N 5/0783* | (2010.01) |
| *C12N 15/86* | (2006.01) |

(52) U.S. Cl.
CPC .......... *C07K 16/2803* (2013.01); *A61K 40/11* (2025.01); *A61K 40/31* (2025.01); *A61K 40/4211* (2025.01); *A61K 40/4215* (2025.01); *A61P 35/00* (2018.01); *C07K 16/2878* (2013.01); *C12N 5/0636* (2013.01); *C12N 15/86* (2013.01); *A61K 2239/28* (2023.05); *A61K 2239/29* (2023.05); *A61K 2239/38* (2023.05); *A61K 2239/46* (2023.05)

(58) Field of Classification Search
CPC .......... C07K 16/2803; C07K 2317/622; A61K 40/11; A61K 40/31; A61K 40/4211; A61K 2239/28; A61K 2239/29; A61K 2239/46; C12N 15/86; C12N 2510/00
See application file for complete search history.

(56) References Cited

U.S. PATENT DOCUMENTS

| | | | |
|---|---|---|---|
| 4,304,639 | A | 12/1981 | Hardy et al. |
| 6,326,193 | B1 | 12/2001 | Liu et al. |
| 11,840,575 | B2 * | 12/2023 | Zhang .................... A61K 40/31 |

FOREIGN PATENT DOCUMENTS

| | | | | |
|---|---|---|---|---|
| CN | 105142677 | A | 12/2015 | |
| CN | 105658671 | A | 6/2016 | |
| CN | 108004259 | A | 5/2018 | |
| CN | 108285489 | A | 7/2018 | |
| CN | 108395478 | A * | 8/2018 | ............. A61K 35/17 |
| CN | 109468283 | A | 3/2019 | |
| CN | 109485734 | A | 3/2019 | |
| TW | 201615832 | A | 5/2016 | |
| WO | 01/29058 | A1 | 4/2001 | |
| WO | 01/96584 | A2 | 12/2001 | |
| WO | 2010104949 | A3 | 11/2010 | |
| WO | WO-2014127261 | A1 * | 8/2014 | ............. A61K 35/17 |
| WO | 2017211900 | A1 | 12/2017 | |

OTHER PUBLICATIONS

Bluhm, Julia et al., "CAR T Cells with Enhanced Sensitivity to B Cell Maturation Antigen for the Targeting of B Cell Non-Hodgkin's Lymphoma and Multiple Myeloma", Molecular Therapy, Aug. 1, 2018, vol. 26, No. 08, pp. 1906-1920.
Zhang Feng et al., "Development in bispecific antibody", Chin J Pharm Anal 2019, 39(1), p. 78-85.

* cited by examiner

*Primary Examiner* — Fereydoun G Sajjadi
*Assistant Examiner* — Masudur Rahman
(74) *Attorney, Agent, or Firm* — NKL Law; Allen Xue

(57) ABSTRACT

Provided are a BCMA-targeting engineered immune cell and the use thereof. In particular, a CAR specifically targeting BCMA is provided. In the CAR, an antigen binding domain contained therein is a J-derived scFv, having an antibody heavy-chain variable region shown in SEQ ID NO: 9, and an antibody light-chain variable region shown in SEQ ID NO: 10. Also provided are a CAR-T cell containing the CAR, and a duplex CAR and CAR T cells containing the J-derived scFv, and related uses thereof. Compared with CAR-T cells constructed by using other scFvs, the CAR-T cells constructed by the present invention have higher killing effects and tumor clearance ability.

16 Claims, 8 Drawing Sheets

Specification includes a Sequence Listing.

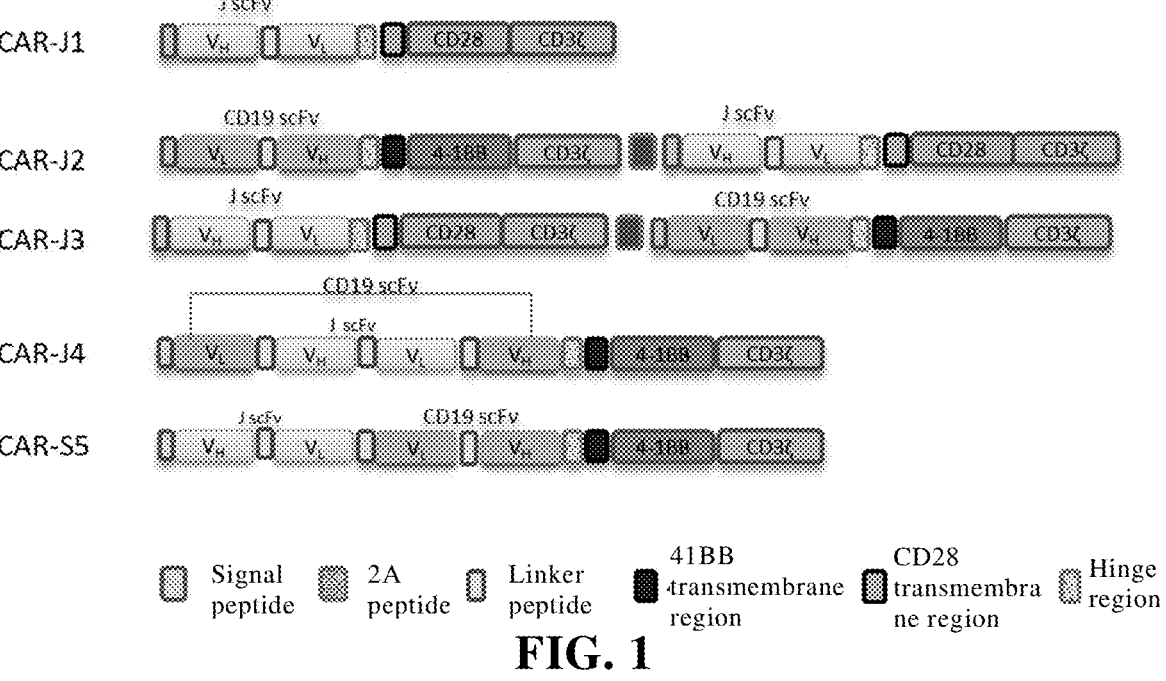
CAR-J1
CAR-J2
CAR-J3
CAR-J4
CAR-S5
Signal peptide    2A peptide    Linker peptide    41BB transmembrane region    CD28 transmembrane region    Hinge region
FIG. 1
Jurkat cell
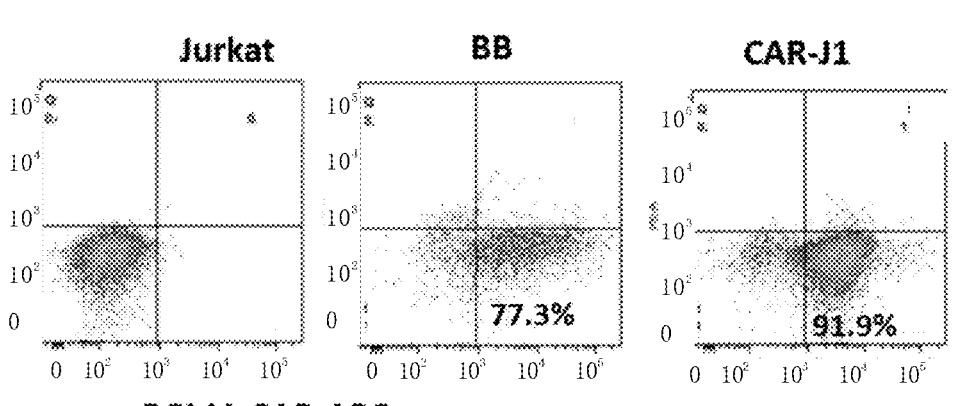
Jurkat    BB    CAR-J1
77.3%    91.9%
BCMA CAR-APC

SEQUENCE LISTING

```
<160> NUMBER OF SEQ ID NOS: 23

<210> SEQ ID NO 1
<211> LENGTH: 22
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: GM-CSF signal peptide

<400> SEQUENCE: 1

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 2
<211> LENGTH: 20
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 2A peptide
```

```
<400> SEQUENCE: 2

Gly Ser Gly Ala Thr Asn Phe Ser Leu Leu Lys Gln Ala Gly Asp Val
1               5                   10                  15

Glu Glu Asn Pro
            20

<210> SEQ ID NO 3
<211> LENGTH: 112
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD3z signal region

<400> SEQUENCE: 3

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 4
<211> LENGTH: 41
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD28 signal region

<400> SEQUENCE: 4

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 5
<211> LENGTH: 42
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 41BB signal region

<400> SEQUENCE: 5

Lys Arg Gly Arg Lys Lys Leu Leu Tyr Ile Phe Lys Gln Pro Phe Met
1               5                   10                  15
```

Arg Pro Val Gln Thr Thr Gln Glu Glu Asp Gly Cys Ser Cys Arg Phe
         20                  25                  30

Pro Glu Glu Glu Glu Gly Gly Cys Glu Leu
         35                  40

<210> SEQ ID NO 6
<211> LENGTH: 27
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD28 transmembrane region

<400> SEQUENCE: 6

Phe Trp Val Leu Val Val Val Gly Gly Val Leu Ala Cys Tyr Ser Leu
1               5                  10                  15

Leu Val Thr Val Ala Phe Ile Ile Phe Trp Val
         20                  25

<210> SEQ ID NO 7
<211> LENGTH: 24
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 transmembrane region

<400> SEQUENCE: 7

Ile Tyr Ile Trp Ala Pro Leu Ala Gly Thr Cys Gly Val Leu Leu Leu
1               5                  10                  15

Ser Leu Val Ile Thr Leu Tyr Cys
         20

<210> SEQ ID NO 8
<211> LENGTH: 45
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 higne region

<400> SEQUENCE: 8

Thr Thr Thr Pro Ala Pro Arg Pro Pro Thr Pro Ala Pro Thr Ile Ala
1               5                  10                  15

Ser Gln Pro Leu Ser Leu Arg Pro Glu Ala Cys Arg Pro Ala Ala Gly
         20                  25                  30

Gly Ala Val His Thr Arg Gly Leu Asp Phe Ala Cys Asp
         35                  40                  45

<210> SEQ ID NO 9
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: J scFv heavy chain

<400> SEQUENCE: 9

-continued

```
Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65              70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Gly Asp Ala Met Asp Tyr Trp Gly Gln
            100                 105                 110

Gly Thr Ser Val Thr Val Ser Ser
        115                 120
```

```
<210> SEQ ID NO 10
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: J scFv light chain

<400> SEQUENCE: 10
```

```
Asp Ile Val Met Thr Gln Ser Gln Arg Phe Met Thr Thr Ser Val Gly
1               5                   10                  15

Asp Arg Val Ser Val Thr Cys Lys Ala Ser Gln Ser Val Asp Ser Asn
            20                  25                  30

Val Ala Trp Tyr Gln Gln Lys Pro Arg Gln Ser Pro Lys Ala Leu Ile
        35                  40                  45

Phe Ser Ala Ser Leu Arg Phe Ser Gly Val Pro Ala Arg Phe Thr Gly
    50                  55                  60

Ser Gly Ser Gly Thr Asp Phe Thr Leu Thr Ile Ser Asn Leu Gln Ser
65              70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105
```

```
<210> SEQ ID NO 11
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: FMC63 scFv heavy chain

<400> SEQUENCE: 11
```

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
```

-continued

```
            35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: FMC63 scFv light chain

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 13
<211> LENGTH: 111
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: BB scFv heavy chain

<400> SEQUENCE: 13

Asp Ile Val Leu Thr Gln Ser Pro Ser Leu Ala Met Ser Leu Gly
1               5                   10                  15

Lys Arg Ala Thr Ile Ser Cys Arg Ala Ser Glu Ser Val Thr Ile Leu
                20                  25                  30

Gly Ser His Leu Ile His Trp Tyr Gln Gln Lys Pro Gly Gln Pro Pro
            35                  40                  45

Thr Leu Leu Ile Gln Leu Ala Ser Asn Val Gln Thr Gly Val Pro Ala
        50                  55                  60

Arg Phe Ser Gly Ser Gly Ser Arg Thr Asp Phe Thr Leu Thr Ile Asp
65                  70                  75                  80
```

-continued

```
Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 14
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: BB scFv light chain

<400> SEQUENCE: 14

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Ala Ala Ala
        115                 120

<210> SEQ ID NO 15
<211> LENGTH: 142
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: April chain

<400> SEQUENCE: 15

Ser Val Leu His Leu Val Pro Ile Asn Ala Thr Ser Lys Asp Asp Ser
1               5                   10                  15

Asp Val Thr Glu Val Met Trp Gln Pro Ala Leu Arg Arg Gly Arg Gly
            20                  25                  30

Leu Gln Ala Gln Gly Tyr Gly Val Arg Ile Gln Asp Ala Gly Val Tyr
        35                  40                  45

Leu Leu Tyr Ser Gln Val Leu Phe Gln Asp Val Thr Phe Thr Met Gly
    50                  55                  60

Gln Val Val Ser Arg Glu Gly Gln Gly Arg Gln Glu Thr Leu Phe Arg
65                  70                  75                  80

Cys Ile Arg Ser Met Pro Ser His Pro Asp Arg Ala Tyr Asn Ser Cys
                85                  90                  95

Tyr Ser Ala Gly Val Phe His Leu His Gln Gly Asp Ile Leu Ser Val
            100                 105                 110

Ile Ile Pro Arg Ala Arg Ala Lys Leu Asn Leu Ser Pro His Gly Thr
        115                 120                 125
```

```
Phe Leu Gly Phe Val Lys Leu Ser Gly Gly Gly Ser Asp Pro
    130                 135                 140

<210> SEQ ID NO 16
<211> LENGTH: 21
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 signal peptide

<400> SEQUENCE: 16

Met Ala Leu Pro Val Thr Ala Leu Leu Leu Pro Leu Ala Leu Leu Leu
1               5                   10                  15

His Ala Ala Arg Pro
            20

<210> SEQ ID NO 17
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: (G4S)3 linker peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 25
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: (G4S)5 linker peptide

<400> SEQUENCE: 18

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 19
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 218 linker peptide

<400> SEQUENCE: 19

Gly Ser Thr Ser Gly Ser Gly Lys Pro Gly Ser Gly Glu Gly Ser Thr
1               5                   10                  15

Lys Gly

<210> SEQ ID NO 20
<211> LENGTH: 335
```

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: EGFRt sequence

<400> SEQUENCE: 20

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
        130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
        290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 21
<211> LENGTH: 49
<212> TYPE: PRT
<213> ORGANISM: Artificial Sequence
<220> FEATURE:
```

-continued

<223> OTHER INFORMATION: synthesized
<220> FEATURE:
<221> NAME/KEY: misc_feature
<223> OTHER INFORMATION: CD8 hinge region

<400> SEQUENCE: 21

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro

<210> SEQ ID NO 22
<211> LENGTH: 47
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 hinge region

<400> SEQUENCE: 22

Ser Gly Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45

<210> SEQ ID NO 23
<211> LENGTH: 113
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD3z signal region

<400> SEQUENCE: 23

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

BCMA-TARGETING ENGINEERED IMMUNE CELL AND USE THEREOF

INCORPORATION OF SEQUENCE LISTING

This application contains a sequence listing in Computer Readable Form (CRF). The CFR file containing the sequence listing entitled "PBA4085109-SequenceListing.txt", which was created on Nov. 5, 2021, and is 19,306 bytes in size. The information in the sequence listing is incorporated herein by reference in entirety.

TECHNICAL FIELD

The invention relates to the field of immunotherapy, in particular to an engineered immune cell targeting BCMA and the use thereof.

BACKGROUND

Multiple myeloma (MM) is a malignant plasma cell tumor. Its tumor cells originate from plasma cells in bone marrow, and plasma cells are cells that develop to the final functional stage of B lymphocytes. Multiple myeloma is basically an incurable disease with the characteristics of high morbidity and high mortality. In the 2017 statistics, there were 30,000 newly diagnosed patients with multiple myeloma in the United States, while 12,000 may face death. At present, the common therapies for multiple myeloma include cytotoxic drugs, protease inhibitors (Bortezomib, etc.), lenalidomide, monoclonal antibodies and corticosteroids, etc. However, they are all partially effective, and the remission cannot be sustained, and the probability of recurrence is very high. Therefore, the improvement of multiple myeloma therapy is particularly important.

Therefore, there is an urgent need in the field for an effective, low recurrence rate and safe multiple myeloma therapy.

SUMMARY OF THE INVENTION

The purpose of the invention is to provide an engineered immune cell targeting BCMA and the use thereof.

Another purpose of the present invention is to provide an engineered immune cell simultaneously targeting CD19 and BCMA and the use thereof.

In a first aspect of the present invention, there is provided a chimeric antigen receptor (CAR) or TCR whose antigen binding domain (scFv) comprises an antibody heavy chain variable region shown in SEQ ID NO: 9, and an antibody light chain variable region shown in SEQ ID NO: 10.

In another preferred embodiment, the scFv also comprises a linker peptide located between the heavy chain variable region and the light chain variable region.

In another preferred embodiment, the scFv is represented by Formula A or Formula B as follows:

$$V_H\text{-}V_L, \tag{A}$$

$$V_L\text{-}V_H, \tag{B}$$

wherein, $V_H$ is the antibody heavy chain variable region; $V_L$ is the antibody light chain variable region; "-" refers to a linker peptide or a peptide bond.

In another preferred embodiment, the linker peptides between the $V_H$ and $V_L$ are 1-4 consecutive sequences shown in SEQ ID NO: 7 (GGGGS), preferably 1-4, more preferably 3-4.

In another preferred embodiment, the structure of the CAR is shown in Formula I:

$$\text{L-scFv-H-TM-C-CD3}\zeta \tag{I}$$

wherein, each "-" is independently a linker peptide or a peptide bond;

L is none or a signal peptide sequence;

H is none or a hinge region;

TM is a transmembrane domain;

C is a co-stimulatory signal molecule;

CD3ζ is a cytoplasmic signal transduction sequence derived from CD3ζ.

In a second aspect of the present invention, there is provided a bispecific CAR or TCR that targets BCMA and a first target, wherein, the antigen binding domain (scFv) targeting BCMA in the bispecific CAR comprises an antibody heavy chain variable region shown in SEQ ID NO: 9, and an antibody light chain variable region shown in SEQ ID NO: 10.

And the first target is selected from the group consisting of:

CD138, Kappa Light Chain, NKG2D-ligands, TACI, GPRC5D, CD2, CD3, CD4, CD5, CD7, CD8, CD19, CD20, CD22, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2 ErbB3, HER-2, HERS, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR (3, TLR7, TLR9, PTCH1, WT-1, Robol, Frizzled, OX40, Notch-1-4, APRIL, CS1, MAGES, Claudin 18.2, Folate receptor α, Folate receptor β, GPC2, CD70, BAFF-R, TROP-2, or a combination thereof.

In another preferred embodiment, the bispecific CAR or TCR contains an antigen binding domain targeting CD19.

In another preferred embodiment, the first target is CD19, and the antigen binding domain (scFv) targeting CD19 in the bispecific CAR comprises an antibody heavy chain variable region shown in SEQ ID NO: 11, and an antibody light chain variable region shown in SEQ ID NO: 12.

In another preferred embodiment, the bispecific CAR comprises both an antigen binding domain targeting the first target and an antigen binding domain targeting the BCMA.

In another preferred embodiment, the structure of the bispecific CAR is shown in Formula II:

$$\text{L-scFv1-I-scFv2-H-TM-C-CD3}\zeta \tag{II}$$

wherein, each "-" is independently a linker peptide or a peptide bond;

L is none or a signal peptide sequence;

I is a flexible linker;

H is none or a hinge region;

TM is a transmembrane domain;

C is a co-stimulatory signal molecule;

CD3ζ is a cytoplasmic signal transduction sequence derived from CD3ζ;

one of scFv1 and scFv2 is the antigen binding domain targeting the first target, and the other is the antigen binding domain targeting BCMA.

In another preferred embodiment, the scFv1 and scFv2 may be independent of each other or in series or in loop structure.

In another preferred embodiment, the scFv1 is an antigen binding domain targeting the first target, and the scFv2 is an antigen binding domain targeting BCMA.

In another preferred embodiment, the scFv1 is an antigen binding domain targeting BCMA, and the scFv2 is an antigen binding domain targeting the first target.

In another preferred embodiment, the sequence of the flexible linker I comprises 1-6, preferably 3-5 consecutive sequences shown in SEQ ID NO: 7 (GGGGS).

In another preferred embodiment, the flexible linker I has the amino acid sequence as shown in SEQ ID NO: 17, 18 or 19.

In another preferred embodiment, the structure of the antigen binding domain targeting the first target is shown in Formula C or Formula D:

$$V_{L1}\text{-}V_{H1} \tag{C};$$

$$V_{H1}\text{-}V_{L1} \tag{D}$$

wherein, $V_{L1}$ is the light chain variable region of the antibody against the first target; $V_{H1}$ is the heavy chain variable region of the antibody against the first target; "-" refers to a linker peptide or a peptide bond.

In another preferred embodiment, the structure of the antigen binding domain targeting CD19 is shown in Formula C or Formula D:

$$V_{L1}\text{-}V_{H1} \tag{C};$$

$$V_{H1}\text{-}V_{L1} \tag{D}$$

wherein, $V_{L1}$ is the light chain variable region of anti-CD19 antibody; $V_{H1}$ is the heavy chain variable region of anti-CD19 antibody; "-" refers to a linker peptide or a peptide bond.

In another preferred embodiment, the antigen binding domain targeting CD19 comprises a heavy chain variable region and a light chain variable region of monoclonal antibody FMC63.

In another preferred embodiment, the heavy chain variable region of anti-CD19 antibody has the amino acid sequence as shown in SEQ ID NO: 11.

In another preferred embodiment, the light chain variable region of anti-CD19 antibody has the amino acid sequence as shown in SEQ ID NO: 12.

In another preferred embodiment, the structure of the antigen binding domain targeting BCMA is shown in Formula A or Formula B:

$$V_{H}\text{-}V_{L}, \tag{A};$$

$$V_{L}\text{-}V_{H}, \tag{B}$$

wherein, $V_{H}$ is the heavy chain variable region of the antibody; $V_{L}$ is the light chain variable region of the antibody; "-" refers to a linker peptide or a peptide bond.

In another preferred embodiment, the scFv1 comprises the antibody heavy chain variable region as shown in SEQ ID NO: 11, and the antibody light chain variable region as shown in SEQ ID NO: 12; and the scFv2 comprises the antibody heavy chain variable region as shown in SEQ ID NO: 9, and the antibody light chain variable region as shown in SEQ ID NO: 10.

In another preferred embodiment, the scFv1 comprises the antibody heavy chain variable region as shown in SEQ ID NO: 9, and the antibody light chain variable region as shown in SEQ ID NO: 10; and the scFv2 comprises the antibody heavy chain variable region as shown in SEQ ID NO: 11, and the antibody light chain variable region as shown in SEQ ID NO: 12.

In another preferred embodiment, the scFv1 and/or scFv2 are mouse, human, human and mouse chimeric, or fully humanized single chain antibody variable region fragments.

In another preferred embodiment, the structure of the bispecific CAR is shown in Formula III or III':

$$L\text{-}V_{L3}\text{-}scFv3\text{-}V_{H3}\text{-}H\text{-}TM\text{-}C\text{-}CD3\zeta \tag{III}$$

$$L\text{-}V_{H3}\text{-}scFv3\text{-}V_{L3}\text{-}H1\text{-}TM\text{-}C\text{-}CD3\zeta \tag{III'}$$

wherein, each "-" is independently a linker peptide or a peptide bond;

elements L, H, TM, C and CD3$\zeta$ are as described above; scFv3 is an antigen binding domain targeting BCMA, $V_{H3}$ is the heavy chain variable region of the antibody against the first target, and $V_{L3}$ is the light chain variable region of the antibody against the first target; or scFv3 is the antigen binding domain targeting the first target, $V_{H3}$ is the heavy chain variable region of anti-BCMA antibody, and $V_{L3}$ is the light chain variable region of anti-BCMA antibody.

In another preferred embodiment, the scFv3 comprises the antibody heavy chain variable region as shown in SEQ ID NO: 9, and the antibody light chain variable region as shown in SEQ ID NO: 10.

In another preferred embodiment, the $V_{H3}$ has the antibody heavy chain variable region as shown in SEQ ID NO: 9, and the $V_{L3}$ has the antibody light chain variable region as shown in SEQ ID NO: 10.

In another preferred embodiment, the scFv3 comprises the antibody heavy chain variable region as shown in SEQ ID NO: 11, and the antibody light chain variable region as shown in SEQ ID NO: 12; and the $V_{H3}$ has the antibody heavy chain variable region as shown in SEQ ID NO: 9, and the $V_{L3}$ has the antibody light chain variable region as shown in SEQ ID NO: 10.

In another preferred embodiment, the scFv3 comprises the antibody heavy chain variable region as shown in SEQ ID NO: 9, and the antibody light chain variable region as shown in SEQ ID NO: 10; and the $V_{H3}$ has the antibody heavy chain variable region as shown in SEQ ID NO: 11, and the $V_{L3}$ has the antibody light chain variable region as shown in SEQ ID NO: 12.

In another preferred embodiment, the structure of the CAR is as shown in FIG. 1.

In another preferred embodiment, the L is a signal peptide of a protein selected from the group consisting of CD8, CD28, GM-CSF, CD4, CD137, or a combination thereof.

In another preferred embodiment, the L is a CD8-derived signal peptide.

In another preferred embodiment, the L has the amino acid sequence as shown in SEQ ID NO: 16 or 1.

In another preferred embodiment, the H is a hinge region of a protein selected from the group consisting of CD8, CD28, CD137, or a combination thereof. In another preferred embodiment, each of the H is independently a CD8-derived hinge region.

In another preferred embodiment, the H has the amino acid sequence as shown in SEQ ID NO: 8.

In another preferred embodiment, the TM is a transmembrane region of a protein selected from the group consisting of CD28, CD3 epsilon, CD45, CD4, CD5, CD8, CD9, CD16, CD22, CD33, CD37, CD64, CD80, CD86, CD134, CD137, CD154, or a combination thereof. In another preferred embodiment, each of the TM is independently a CD8-derived or CD28-derived transmembrane region. In another preferred embodiment, the CD8-derived transmembrane region has the amino acid sequence as shown in SEQ ID NO: 7.

In another preferred embodiment, the CD28-derived transmembrane region has the amino acid sequence as shown in SEQ ID NO: 6.

In another preferred embodiment, the C is a co-stimulatory signal molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, or a combination thereof. In another preferred embodiment, the C is a CD28-derived and/or 4-1BB-derived co-stimulatory signal molecule.

In another preferred embodiment, the 4-1BB-derived co-stimulatory signal molecule has the amino acid sequence as shown in SEQ ID NO: 5.

In another preferred embodiment, the CD28-derived co-stimulatory signal molecule has the amino acid sequence as shown in SEQ ID NO: 4.

In another preferred embodiment, the CD3ζ has the amino acid sequence as shown in SEQ ID NO: 3.

In another preferred embodiment, the CAR (preferably C-terminal or N-terminal) further comprises a cell suicide element.

In another preferred embodiment, the cell suicide element is linked to the L or CD3ζ of the CAR or the bispecific CAR via T2A.

In a third aspect of the present invention, there is provided a nucleic acid molecule encoding the CAR or TCR of the first aspect of the present invention or the bispecific CAR or TCR of the second aspect of the present invention.

In a fourth aspect of the present invention, there is provided a vector comprising the nucleic acid molecule of the third aspect of the present invention.

In another preferred embodiment, the vector is selected from the group consisting of DNA, RNA, plasmids, lentiviral vectors, adenoviral vectors, retroviral vectors, transposons, or a combination thereof.

In another preferred embodiment, the vector is a lentiviral vector.

In a fifth aspect of the present invention, there is provided a host cell comprising the vector of the fourth aspect of the present invention, or having the exogenous nucleic acid molecule of the third aspect of the present invention integrated in the chromosome, or expressing the CAR or TCR of the first aspect of the present invention or the bispecific CAR or TCR of the second aspect of the present invention.

In a sixth aspect of the present invention, there is provided an engineered immune cell comprising the vector of the fourth aspect of the present invention, or having the exogenous nucleic acid molecule of the third aspect of the present invention integrated in the chromosome, or expressing the CAR or TCR of the first aspect of the present invention or the bispecific CAR or TCR of the second aspect of the present invention.

In another preferred embodiment, the immune cell has one or more characteristics selected from the group consisting of:

(a) the expression of PD-1 gene of the immune cell is silenced;

(b) the immune cell is a T cell, and the expression of TCR gene of the T cell is silenced; and (c) the immune cell expresses an exogenous cell suicide element;

(d) the immune cell expresses or secretes PD-1 antibodies, PD-L1 antibodies, CD47 antibodies, Tim3 antibodies, Lag3 antibodies, Tigit antibodies, OX40 antibodies, ICOS antibodies, IL7, CXCL19, IL21, IL15, IL2, IL18, or a combination thereof; and (e) cytokine-related signaling pathways of the immune cell are enhanced, wherein the cytokine is selected from the group consisting of IL7, CXCL19, IL21, IL15, IL2, IL18, or a combination thereof.

In another preferred embodiment, the engineered immune cell is selected from the group consisting of:

(i) a chimeric antigen receptor T cell (CAR-T cell); or (ii) a chimeric antigen receptor NK cell (CAR-NK cell).

In another preferred embodiment, the immune cell expresses exogenous cell suicide elements.

In another preferred embodiment, the CAR is co-expressed with the cell suicide element in the immune cell.

In another preferred embodiment, the CAR is connected to the cell suicide element via a self-shearing element.

In another preferred embodiment, the cell suicide element is located at the N-terminal or C-terminal of the CAR.

In another preferred embodiment, the self-shearing element comprises a 2A sequence or an IRES sequence, preferably P2A and T2A.

In another preferred embodiment, the cell suicide element is selected from the group consisting of HSV-TK, iCasp9, ΔCD20, mTMPK, ΔCD19, RQR8, EGFRt, or a combination thereof.

In another preferred embodiment, the structure of the cell suicide element is shown in the Formula IV:

$$L2\text{-}D\text{-}F \qquad\qquad\qquad (IV)$$

wherein, each "-" is independently a linker peptide or a peptide bond;

L2 is an optional signal peptide sequence;

D is a suicide switch element;

F is a transmembrane element.

In another preferred embodiment, the signal peptide is a signal peptide derived from GM-CSFR.

In another preferred embodiment, the cell suicide element is selected from the group consisting of truncated epidermal growth factor receptor (EGFRt), truncated CD19 (CD19t) gene, induced caspase 9 gene (iCasp9), HSV-TK, ΔCD20, mTMPK, or a combination thereof.

In another preferred embodiment, the cell suicide element is EGFRt.

In another preferred embodiment, the engineered immune cell is used for autologous immunotherapy and/or allogeneic immunotherapy.

In another preferred embodiment, the engineered immune cells can kill tumor cells with clonal proliferation ability.

In another preferred embodiment, the immune cell expressing the bispecific CAR of the second aspect of the present invention has a longer in vivo survival time than the immune cell expressing the CAR of the first aspect of the present invention.

In another preferred embodiment, the in vivo includes autologous in vivo or allogeneic in vivo.

In a seventh aspect of the present invention, there is provided an engineered immune cell comprising an exogenous first expression cassette and a second expression cassette, wherein the first expression cassette is used for expressing a first CAR or a first exogenous TCR targeting the first target, the second expression cassette is used for expressing a second CAR or a second exogenous TCR targeting BCMA;

or the immune cell expresses the first CAR or the first exogenous TCR targeting the first target and the second CAR or the second exogenous TCR targeting BCMA;

wherein, the antigen binding domain (scFv) targeting BCMA in the second CAR or the second exogenous TCR comprises an antibody heavy chain variable region shown in SEQ ID NO: 9, and an antibody light chain variable region shown in SEQ ID NO: 10;

and the first target is selected from the following group: CD138, Kappa Light Chain, NKG2D-ligands, TACI, GPRC5D, CD2, CD3, CD4, CD5, CD7, CD8, CD19, CD20, CD22, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2 ErbB3, HER-2, HERS, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR (3, TLR7, TLR9, PTCH1, WT-1, Robol, Frizzled, OX40, Notch-1-4, APRIL, CS1, MAGES, Claudin 18.2, Folate receptor α, Folate receptor β, GPC2, CD70, BAFF-R, TROP-2, or a combination thereof.

In another preferred embodiment, the first target is CD19, and the antigen binding domain (scFv) targeting CD19 in the first CAR comprises an antibody heavy chain variable region shown in SEQ ID NO: 11, and an antibody light chain variable region shown in SEQ ID NO: 12.

In another preferred embodiment, the second CAR is the CAR described in the first aspect of the present invention.

In another preferred embodiment, the first CAR and the second CAR are located on the cell membrane of the immune cell.

In another preferred embodiment, a first CAR targeting CD19 and a second CAR targeting BCMA are expressed on the cell membrane of the immune cell.

In another preferred embodiment, the first expression cassette and the second expression cassette are located on the same or different vectors.

In another preferred embodiment, the first expression cassette and the second expression cassette are located in the same vector.

In another preferred embodiment, the structure of the first CAR is shown in the following Formula V:

L-scFv1'-H-TM-C-CD3ζ　　　　(V)

wherein,
each "-" is independently a linker peptide or a peptide bond;
elements L, H, TM, C and CD3ζ are as described above; scFv1' is an antigen binding domain targeting CD19.

In another preferred embodiment, the first CAR and the second CAR are linked by a 2A peptide.

In another preferred embodiment, the sequence of the 2A peptide is as shown in SEQ ID NO: 2.

In another preferred embodiment, the immune cell also include cell suicide elements.

In another preferred embodiment, the cell suicide element is connected (or tandem) with the bispecific CAR via T2A.

In another preferred embodiment, the cell suicide element is connected with the first CAR and/or the second CAR via T2A.

In another preferred embodiment, the expression of PD-1 gene of the immune cell is silenced.

In another preferred embodiment, "the expression of PD-1 gene is silenced" means that PD-1 gene is not expressed or low-expressed.

In another preferred embodiment, the "low-expressed" refers to the ratio of the level of PD-1 gene expression G1 of the immune cell to the level of PD-1 gene expression G0 of the normal immune cell, i.e. G1/G0≤0.5, preferably G1/G0≤0.3, more preferably ≤0.2, more preferably ≤0.1, and most preferably 0.

In another preferred embodiment, the "low-expressed" refers to the ratio of the level of PD-1 gene expression G1 of the CAR-T cell to the level of PD-1 gene expression G0 of the normal T cell, i.e. G1/G0≤0.5, preferably G1/G0≤0.3, more preferably ≤0.2, more preferably ≤0.1, and most preferably 0.

In an eighth aspect of the present invention, there is provided a preparation comprising the CAR or TCR according to the first or second aspects of the present invention, or the engineered immune cell according to the sixth or seventh aspects of the present invention, and a pharmaceutically acceptable carrier, diluent or excipient.

In another preferred embodiment, the preparation is a liquid preparation.

In another preferred embodiment, the dosage form of the preparation is an injection.

In another preferred embodiment, the concentration of the engineered immune cells in the preparation is $1\times10^3$-$1\times10^8$ cells/ml, preferably $1\times10^4$-$1\times10^7$ cells/ml.

In another preferred embodiment, the CAR comprises a bispecific CAR.

In a ninth aspect of the present invention, there is provided a use of the CAR or TCR according to the first or second aspects of the present invention, or the engineered immune cell according to the sixth or seventh aspects of the present invention for the preparation of a drug or preparation for the prevention and/or treatment of cancer or tumor.

In another preferred embodiment, the tumor is a hematological tumor.

In another preferred embodiment, the hematological tumor is selected from the group consisting of acute myeloid leukemia (AML), multiple myeloma (MM), chronic lymphocytic leukemia (CLL), acute lymphoblastic leukemia (ALL), diffuse large B-cell lymphoma (DLBCL), or a combination thereof.

In another preferred embodiment, the cancer or tumor is multiple myeloma.

In another preferred embodiment, the cancer or tumor is lymphoma.

In another preferred embodiment, the lymphoma is selected from the following group: Hodgkin's lymphoma (HL), diffuse large B-cell lymphoma (DLBCL), follicular lymphoma (FL), chronic lymphocyte leukocyte (CLL), small lymphocyte lymphoma (SLL), marginal zone lymphoma (MZL), mantle cell lymphoma (MCL), Burkitt's lymphoma (BL), and complex B-cell non-Hodgkin's lymphoma.

In another preferred embodiment, the cancer or tumor comprises a recurrent cancer or tumor.

In another preferred embodiment, the drug or preparation treats cancer or tumor by killing tumor cells having clonal proliferating ability.

In another preferred embodiment, the tumor cells having clone proliferating ability comprise clone forming cells, tumor cell precursor cells, and tumor progenitor cells.

In a tenth aspect of the present invention, there is provided a method for preparing engineered immune cells which express the CAR or TCR according to the first aspect or the second aspect of the present invention, comprising the following steps: transferring the nucleic acid molecules according to the third aspect of the present invention or the vectors according to the fourth aspect of the present invention into the immune cells to obtain the engineered immune cells.

In another preferred embodiment, the immune cells are T cells or NK cells.

In an eleventh aspect of the present invention, there is provided a method for preparing engineered immune cells, comprising the steps of:

(1) providing an immune cell to be modified; and (2) introducing a first expression cassette for expressing a first CAR targeting the first target into the immune cell; and (3) introducing a second expression cassette for expressing a second CAR targeting BCMA into the immune cell to obtain the engineered immune cell, wherein, the antigen binding domain (scFv) targeting BCMA in the second CAR comprises an antibody heavy chain variable region shown in SEQ ID NO: 9, and an antibody light chain variable region shown in SEQ ID NO: 10;

and the first target is selected from the following group: CD138, Kappa Light Chain, NKG2D-ligands, TACI, GPRC5D, CD2, CD3, CD4, CD5, CD7, CD8, CD19, CD20, CD22, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2 ErbB3, HER-2, HERS, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR (3, TLR7, TLR9, PTCH1, WT-1, Robol, Frizzled, OX40, Notch-1-4, APRIL, CS1, MAGES, Claudin 18.2, Folate receptor α, Folate receptor β, GPC2, CD70, BAFF-R, TROP-2, or a combination thereof.

In another preferred embodiment, the step (2) may be performed before, after, simultaneously or alternately with the step (3).

In another preferred embodiment, step (2) or step (3) may be omitted when the immune cell to be modified in step (1) has expressed the first CAR or the second CAR.

In a twelfth aspect of the invention, there is provided a kit for preparing the engineered immune cells according to the sixth or seventh aspects of the present invention, and the kit contains a container and the nucleic acid molecule according to the third aspect of the present invention, or the vector according to the fourth aspect of the present invention, located in the container.

In a thirteenth aspect of the present invention, there is provided a kit for preparing the engineered immune cells of the sixth or seventh aspects of the present invention, and the kit comprises a container, and which located in the container comprising:

(1) a first nucleic acid sequence comprising a first expression cassette for expressing the first CAR targeting the first target; and (2) a second nucleic acid sequence comprising a second expression cassette for expressing the second CAR targeting BCMA;

wherein, the antigen binding domain (scFv) targeting BCMA in the second CAR comprises an antibody heavy chain variable region shown in SEQ ID NO: 9, and an antibody light chain variable region shown in SEQ ID NO: 10;

and the first target is selected from the following group: CD138, Kappa Light Chain, NKG2D-ligands, TACI, GPRC5D, CD2, CD3, CD4, CD5, CD7, CD8, CD19, CD20, CD22, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2 ErbB3, HER-2, HERS, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR (3, TLR7, TLR9, PTCH1, WT-1, Robol, Frizzled, OX40, Notch-1-4, APRIL, CS1, MAGES, Claudin 18.2, Folate receptor α, Folate receptor β, GPC2, CD70, BAFF-R, TROP-2, or a combination thereof.

In another preferred embodiment, the first and second nucleic acid sequences are located in the same or different containers.

In another preferred embodiment, the first and second nucleic acid sequences are located on the same expression vector.

In a fourteenth aspect of the present invention, there is provided a use of the engineered immune cells according to the sixth or seventh aspects of the present invention for the prevention and/or treatment of cancer or tumor.

In another preferred embodiment, the cancer or tumor is multiple myeloma.

In a fifteenth aspect of the present invention, there is provided a method for treating a disease, comprising administering to a subject in need of treatment an appropriate amount of the cells according to the sixth or seventh aspects of the present invention, or the preparation according to the fifth aspect of the present invention.

In another preferred embodiment, the disease is cancer or tumor.

In a sixteenth aspect of the present invention, there is provided a method for enhancing viability of immune cells in vivo or killing ability of immune cells to tumor cells with clonal proliferation ability, comprising (a) simultaneously expressing an exogenous first expression cassette and a second expression cassette in the immune cell, wherein the first expression cassette is used for expressing the first CAR targeting CD19 and the second expression cassette is used for expressing the second CAR targeting BCMA; or (b) expressing the bispecific CAR of the second aspect in the immune cells.

In another preferred embodiment, the immune cells constructed by the method are as described in the sixth and seventh aspects of the present invention.

In another preferred embodiment, the first expression cassette and the second expression cassette have the same meaning as the first expression cassette and the second expression cassette in the seventh aspect of the present invention.

In another preferred embodiment, the in vivo includes autologous in vivo or allogeneic in vivo.

In a seventeenth aspect of the present invention, there is provided a method for enhancing viability of engineered immune cells targeting BCMA in vivo or killing ability to tumor cells with clonal proliferating ability, comprising expressing an exogenous first expression cassette in the engineered immune cells, and the first expression cassette is used for expressing the first CAR targeting CD19.

In another preferred embodiment, the first expression cassette has the same meaning as the first expression cassette and the second expression cassette in the seventh aspect of the present invention.

In another preferred embodiment, the engineered immune cells targeting BCMA are immune cells expressing the CAR of the first aspect of the present invention.

In another preferred embodiment, the in vivo includes autologous in vivo or allogeneic in vivo.

In an eighteenth aspect of the present invention, there is provided a use of a first expression cassette, which is used for expressing the first CAR targeting CD19, for enhancing the viability of engineered immune cells targeting BCMA in vivo or killing ability of tumor cells with clonal proliferation ability, or, for preparing a kit for enhancing the viability of engineered immune cells targeting BCMA in vivo or the killing ability of tumor cells with clonal proliferating ability.

In another preferred embodiment, the in vivo includes autologous in vivo or allogeneic in vivo.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

DESCRIPTION OF DRAWINGS

FIG. 1 shows a schematic structural diagram of the CAR of the present invention.

FIG. 13A shows the expression of BCMA antigen on the surface of Raji lymphoma target cells, and FIG. 13B shows the killing of CAR-J1 cells on Raji lymphoma target cells under different E:T ratios.

DETAILED DESCRIPTION

Figure 2:
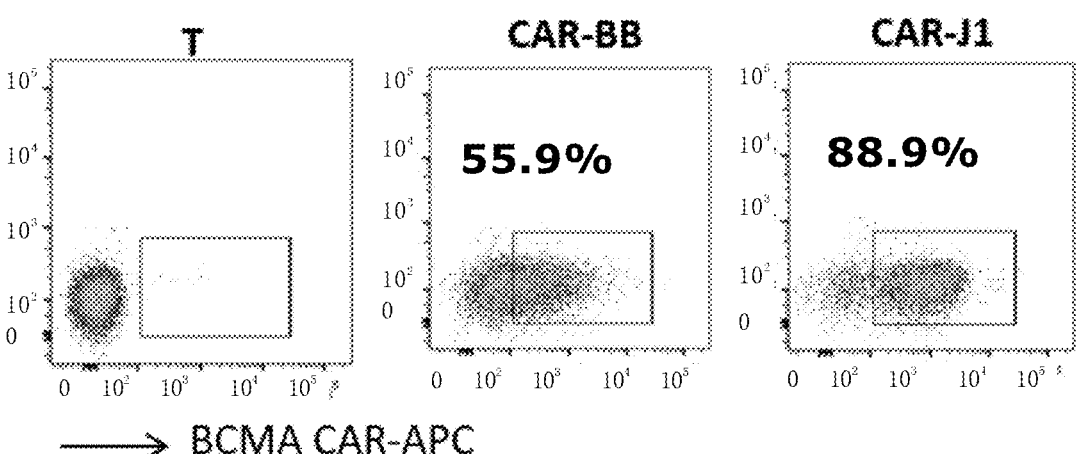
FIG. 2 shows the results of flow cytometry analysis of the expression of CAR-BB and CAR-J1 on the surface of Jurkat cells and primary T cells respectively in the present invention.

After extensive and in-depth research, the inventor constructed a new engineered immune cell targeting BCMA for the first time, and the antigen binding domain in CAR contained in it is J-derived scFv. Experiments show that compared with CAR-T cells constructed by using BB scFv and BCMA binding domain derived from April, CAR-T cells constructed in the present invention have higher killing effect and tumor elimination ability. The present invention also constructs the dual CAR-T cells using J scFv and CD19 scFv, which are CAR-T cells can kill BCMA and CD19 positive cells at the same time.

In particular, the present invention utilizes scFv of different BCMA antibodies to construct CAR-T cells and compares them, and unexpectedly finds that CAR-T cells constructed by scFv derived from J have higher ability to kill BCMA over-expressed cells and BCMA positive tumor target cells than that constructed by scFv of BB and BCMA binding domain derived from April. In the in vivo mouse models, it also shows higher tumor elimination ability than BB-derived CAR-T. CAR-T cells constructed with other scFv targeting BCMA that are common in the art do not show ideal in vitro and in vivo functions.

The Terms

In order to make it easier to understand the present disclosure, certain terms are first defined. As used herein, each of the following terms shall have the meanings given below unless expressly provided herein. Other definitions are stated throughout the application.

The term "about" may refer to a value or composition within an acceptable error range of a particular value or composition determined by those of ordinary skill in the art, which will depend in part on how the value or composition is measured or determined.

The term "administration" refers to the physical introduction of the product of the present invention into a subject using any of various methods and delivery systems known to those skilled in the art, including intravenous, intramuscular, subcutaneous, intraperitoneal, spinal or other parenteral routes of administration, such as by injection or infusion.

The term "antibody" (Ab) shall include, but is not limited to an immunoglobulin, that specifically binds to an antigen and comprises at least two heavy (H) chains and two light (L) chains interconnected by disulfide bonds, or an antigen-binding portion thereof. Each H chain contains a heavy chain variable region (abbreviated herein as $V_H$) and a heavy chain constant region. The heavy chain constant region contains three constant domains, CH1, CH2 and CH3. Each light chain contains a light chain variable region (abbreviated herein as VL) and a light chain constant region. The light chain constant region contains a constant domain CL. The VH and VL regions can be further subdivided into hypervariable regions called complementary determination regions (CDR), which are interspersed within more conservative regions called frame regions (FR). Each VH and VL contains three CDRs and four FRs, which are arranged from amino terminal to carboxyl terminal in the following order: FR1, CDR1, FR2, CDR2, FR3, CDR3, FR4. The variable regions of heavy and light chains contain binding domains that interact with an antigen.

It should be understood that the amino acid names herein are identified by international single English letters, and the corresponding three English letter abbreviations of amino acid names are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V).

B Cell Maturation Antigen (BCMA)

BCMA is a transmembrane protein expressed on the surface of mature B lymphocytes, i.e., plasmablasts and plasma cells. And multiple myeloma is caused by abnormal proliferation of plasma cells and invasion of bone marrow. Studies have shown that BCMA is expressed on multiple myeloma cells. Car-T cells targeting BCMA have been proved to be able to kill myeloma cells specifically. However, some patients still have recurrence after receiving CAR-T cell therapy targeting BCMA. For these patients with recurrence, it is necessary to find another target that is different from BCMA in order to continue treatment.

CD19

CD19 molecule is a transmembrane protein on the surface of B cells, which is closely related to B cell activation, signal transduction and growth regulation. As shown in FIG. 1, CD19 is expressed on the surface of almost all B cells, and CAR-T cells targeting CD19 are effective in the treatment of leukemia and lymphoma at present. It is generally believed that 99.95% of plasma cells do not express CD19 on their surfaces, so the possibility of CD19 being used to treat multiple myeloma is ignored.

Chimeric Antigen Receptor (CAR)

The chimeric antigen receptor (CAR) of the present invention includes an extracellular domain, a transmembrane domain, and an intracellular domain. The extracellular domain includes a target-specific binding element (also known as an antigen binding domain). The intracellular domain includes a costimulatory signal transduction region and a chain. The costimulatory signal transduction region refers to a part of the intracellular domain including costimulatory molecules. The costimulatory molecules are cell surface molecules needed by lymphocytes to respond effectively to antigens, rather than antigen receptors or their ligands.

Linkers may be incorporated between the extracellular domain and the transmembrane domain of the CAR, or between the cytoplasmic domain and the transmembrane domain of the CAR. As used herein, the term "linker" generally refers to any oligopeptide or polypeptide that functions to link the transmembrane domain to the extracellular domain or cytoplasmic domain of a polypeptide chain. The linker may comprise 0 to 300 amino acids, preferably 2 to 100 amino acids and most preferably 3 to 50 amino acids.

In a preferred embodiment of the present invention, the extracellular domain of the CAR provided by the present invention comprises an antigen binding domain targeting BCMA (or BCMA and CD19). When the CAR of the present invention is expressed in T cells, it can perform antigen recognition based on the antigen binding specificity. When it binds to its associated antigen, it affects tumor cells, causing tumor cells not to grow, being prompted to die or being affected in other ways, and causing the patient's tumor burden to be reduced or eliminated. The antigen binding domain is preferably fused with an intracellular domain derived from one or more of the costimulatory molecule and chain. Preferably, the antigen binding domain is fused with the intracellular domain of the combination of the 4-1BB signaling domain and CD3ζ signaling domain.

As used herein, "antigen binding domain" and "single chain antibody fragment" all refer to a Fab fragment, a Fab'fragment, a F (ab')$_2$ fragment, or a single Fv fragment having antigen binding activity. The Fv antibody contains the variable region of the heavy chain and the variable region of the light chain, but does not have the constant region, and has the smallest antibody fragment with all the antigen binding sites. Generally, the Fv antibody also contains a polypeptide linker between VH and VL domains, and can form the structure required for antigen binding. The antigen binding domain is usually a scFv (single-chain variable fragment). The size of scFv is generally ⅙ of that of a complete antibody. The single chain antibody is preferably an amino acid chain sequence encoded by a nucleotide chain. As a preferred embodiment of the present invention, the antigen-binding domain comprises an antibody specifically recognizing BCMA and optionally an antibody specifically recognizing CD19, preferably a single chain antibody.

For the hinge region and transmembrane region (transmembrane domain), the CAR may be designed to include a transmembrane domain fused to the extracellular domain of the CAR. In one embodiment, a transmembrane domain naturally associated with one of the domains in the CAR is used. In some examples, the transmembrane domain may be selected or modified by amino acid substitution to avoid binding such a domain to transmembrane domains of the same or different surface membrane proteins, thereby minimizing interaction with other members of the receptor complex.

The intracellular domains in the CAR of the present invention include a signal transduction domain of 4-1BB and a signal transduction domain of CD3ζ.

Preferably, the CAR of the present invention also including cell suicide elements.

Preferably, the scFv targeting BCMA of the present invention is J scFv, and the BB scFv and April chain in the examples serve as a control. BB scFv and April chain are commonly used binding sequences targeting BCMA in the field. BB scFv is described in PCT application WO 2010104949 A3, and April chain is described in CN105658671A.

Bispecific CAR Targeting CD19 and BCMA

Multiple myeloma (MM) is a malignant plasma cell tumor. Its tumor cells originate from plasma cells in bone marrow, and plasma cells are cells that develop to the final functional stage of B lymphocytes. Multiple myeloma is basically an incurable disease with the characteristics of high morbidity and high mortality. In the 2017 statistics, there were 30,000 newly diagnosed patients with multiple myeloma in the United States, while 12,000 may face death. At present, the common therapies for multiple myeloma include cytotoxic drugs, protease inhibitors (Bortezomib, etc.), lenalidomide, monoclonal antibodies and corticosteroids, etc. However, they are all partially effective, and the remission cannot be sustained, and the probability of recurrence is very high. Therefore, the improvement of multiple myeloma therapy is particularly important.

CD19, a glycoprotein with a molecular weight of 95 kDa, is expressed on the membrane surface of preB cells and mature B cells. It is closely related to the transmembrane conduction pathway of Ca++ in B cells and regulates the proliferation and differentiation of B cells. CD19 is mainly expressed in normal B cells and cancerous B cells, with high tissue expression specificity, so it is a good antibody or CAR-T immunotherapy target. However, in the process of immunotherapy, the CD19 epitope of B cells is often lost, resulting in no response to immunotherapy or recurrence of patients.

Bispecific means that the same CAR can specifically bind and recognize two different antigens, and CAR can produce immune response when binding to any antigen.

In another preferred embodiment, the bispecific CAR targeting CD19 and BCMA is as described in the second aspect of the present invention.

In a preferred embodiment of the present invention, the extracellular domain of the CAR provided by the present invention comprises antigen binding domains targeting CD19 and BCMA, including anti-CD19 scFv and anti-BCMA scFv.

In another preferred embodiment, the present invention provides a bispecific chimeric antigen receptor for CD19 and BCMA antigens. The structural components of the CAR targeting both CD19 and BCMA may comprises a signal peptide, an anti-CD19 scFv, an anti-BCMA scFv, a hinge region, a transmembrane region, and an intracellular T cell signal region, wherein CD19scFv and BCMAscFv are connected by a short peptide segment (G4S)xN. The structure of the CAR targeting both CD19 and BCMA is described in the second aspect of the present invention.

In another preferred embodiment, the CD19 and BCMA bispecific CAR of the present invention is a single structure comprising scFv against CD19 and BCMA. Wherein CAR includes CD19 scFv and BCMA scFv, and the sequences of CD19 scFv and BCMA scFv and the hinge are the main factors affecting its function.

In another preferred embodiment, the present invention optimizes the sequence of the BCMA scFv, and the BCMA scFv (J scFv) has high affinity and good specificity with BCMA, and can specifically target the full-length antigen and extracellular region of BCMA.

In a preferred embodiment of the present invention, (G4S)x3 is used to connect CD19scFv and BCMAscFv, at this time, the activity and lethality of CAR are the best.

Compared with the CAR targeting a single antigen, the CAR using bidirectional targeting CD19 and BCMA has significantly enhanced affinity, significantly increased activity of immune cells and synergistic effect. In addition, due to the uneven expression levels of CD19 and BCMA in tumor cells, the scope of dual-targeted CAR-T therapy is wider. CAR-immune cells targeting both CD19 and BCMA can reduce the possibility of antigen escape caused by down-regulation or deletion of single surface antigen.

Chimeric Antigen Receptor T Cells (CAR-T Cells)

As use herein, the terms "CAR-T cell", "CAR-T", "CAR-T cell of the present invention" include CAR-T cells of the third aspect of the present invention.

CAR-T cells have the following advantages over other T cell-based therapies: (1) the action process of CAR-T cells is not limited by MHC; (2) since many tumor cells express the same tumor antigen, once the CAR gene for a certain tumor antigen is constructed, it can be widely used; (3) CAR can use both tumor protein antigen and glycolipid non-protein antigen, thereby expanding the target range of tumor antigens; (4) the use of autologous cells from patients reduces the risk of rejection reaction; (5) CAR-T cells have immune memory function and can survive in vivo for a long time.

Chimeric Antigen Receptor NK Cells (CAR-NK Cells)

As use herein, the terms "CAR-NK cell", "CAR-NK", "CAR-NK cell of the present invention" all refer to the CAR-NK cells of the third aspect of the present invention. The CAR-NK cells of the present invention can be used for treating tumors with high expression of BCMA, such as multiple myeloma and the like.

Natural killer (NK) cells are a major class of immune effector cells, which protect the body from virus infection and invasion of tumor cells through non-antigen-specific pathways. Engineered (genetically modified) NK cells may obtain new functions, including the ability to specifically recognize tumor antigens and enhance anti-tumor cytotoxicity.

Compared with autologous CAR-T cells, CAR-NK cells also have the following advantages, for example: (1) they kill tumor cells directly by releasing perforin and granzyme, but have on killing effect on normal cells of the body; (2) they release a small amount of cytokines, thus reducing the risk of cytokine storms; (3) they are easy to expand in vitro and can be developed into "off-the-shelf" products. In addition, it is similar to CAR-T cell therapy.

Suicide Gene Switch

In order to further control the defects such as non-tumor targeting of CAR-T cells and cytokine release syndrome, all CART cells of the present invention are provided with suicide gene switches, which can effectively eliminate CAR-T cells in the body and block unknown or uncontrollable long-term toxicity under the action of exogenous drugs, so as to ensure the patients safety.

The suicide switch used in the present invention can be herpes simplex virus thymidine kinase (HSV-TK), inducible caspase 9 (iCasp9), CD20, mutated human thymidylate kinase (mTMPK), etc. In comparison, HSV-TK, iCasp9 and CD20 have the same clearance ability on CAR-cells, but the clearance of iCasp9 and CD20 is faster, and HSV-TK is slower.

The iCasp9 suicide switch contains a FKBP12-F36V domain, which can be linked to cysteine aspartate proteinase 9 through a flexible linker, which does not contain recruitment domain. FKBP12-F36V contains a FKBP domain in which phenylalanine replaces valine at the 36th amino acid residue. It has high selectivity and sub-nanomolar affinity, and can be combined with dimerization to form a ligand, such as other inert small molecules AP1903. When small molecules are added, it can promote its dimerization, thus inducing apoptosis of cells, but it is ineffective for normal cells without a suicide switch.

Induced safety switch caspase9 (iCasp9) uses human caspase9 to fuse FK506 binding protein (FKBP), so that it can be induced to form dimer by chemical inducer (AP1903/Rimiducid, Bellicum Pharmaceutical), which leads to apoptosis of cells expressing the fusion protein.

Although CD19 and BCMA are highly expressed in tumor cells, they are also expressed in normal B cells. The engineered immune cells of the present invention will attack normal B cells in the body.

How to control the safety of CAR-cells has always been an urgent problem to be solved. Adding a safety switch to the CAR-cell is the safest way to stop the activity of CAR-cells. The inducible iCasp9 safety switch controls CAR-cell clearance after CAR-cells produce severe toxicity (CRS/neurotoxicity) or after patients achieve long-term sustained remission.

Vector

The nucleic acid sequence encoding the desired molecule can be obtained using recombinant methods known in the art, such as, for example, by screening a library from a cell expressing the gene, by obtaining the gene from a vector known to comprise the gene, or by directly isolating from cells and tissues containing the gene using standard techniques. Alternatively, the gene of interest can be synthesized and produced.

The present invention also provides a vector in which the expression cassette of the invention is inserted. Vectors derived from retroviruses such as lentivirus are suitable tools for long-term gene transfer because they allow long-term stable integration of transgenes and their proliferation in daughter cells. Lentiviral vectors have advantages over vectors derived from onco-retroviruses such as murine leukemia viruses in that they can transduce non-proliferating cells, such as hepatocytes. They also have the advantage of low immunogenicity.

In brief summary, the expression cassette or nucleic acid sequence of the present invention is generally operably linked to a promoter and incorporated into an expression vector. The vector is suitable for replication and integration in eukaryotes. Typical cloning vectors contain transcriptional and translational terminators, initial sequences, and promoters that can be used to regulate the expression of desired nucleic acid sequences.

The expression constructs of the present invention can also be used for nucleic acid immunization and gene therapy, using standard gene delivery protocols. Methods for gene delivery are known in the art. See, for example, U.S. Pat. Nos. 5,399,346, 5,580,859, 5,589,466, which are incorporated herein in its entirety by reference. In another embodiment, the present invention provides a gene therapy vector.

The nucleic acid can be cloned into many types of vectors. For example, the nucleic acid may be cloned into vectors including, but not limited to, plasmids, phage particles, phage derivatives, animal viruses, and clay particles. Specific vectors of interest include expression vectors, replication vectors, probe production vectors, and sequencing vectors.

Further, the expression vector may be provided to cells in the form of a viral vector. Viral vector techniques are well known in the art and are described, for example, in Sambrook et al. (2001, Molecular Cloning: A Laboratory Manual, Cold Spring Harbor Laboratory, New York) and other manuals of virology and molecular biology. Viruses that can be used as vectors include, but are not limited to, retroviruses, adenoviruses, adeno-associated viruses, herpesviruses, and lentivirus. Typically, a suitable vector comprises a replication origin, a promoter sequence, a convenient restriction enzyme site, and one or more selectable markers that function in at least one organism (e.g. WO01/96584; WO01/29058; and U.S. Pat. No. 6,326,193).

Many virus-based systems have been developed for transferring genes into mammalian cells. For example, retroviruses provide a convenient platform for gene delivery systems. The selected gene may be inserted into a vector and packaged into a retroviral particle using techniques known in the art. The recombinant virus can then be isolated and transmitted to target cells either in vivo or ex vivo. Many retroviral systems are known in the art. In some embodiments, adenovirus vectors are used. Many adenovirus vectors are known in the art. In one embodiment, lentiviral vectors are used.

Additional promoter elements, e.g., enhancers, may regulate the frequency of transcription initiation. Typically, these are located in the 30-110 bp region upstream of the initiation site although it has recently been shown that many promoters also contain functional elements downstream of the initiation site. The spacing between promoter elements is often flexible to maintain promoter function when the element is inverted or moved relative to the other. In the thymidine kinase (tk) promoter, the spacing between promoter elements can be increased by 50 bp apart before activity begins to decline. Depending on the promoter, it is shown that individual elements can function either cooperatively or independently to initiate transcription.

One example of a suitable promoter is the immediate early cytomegalovirus (CMV) promoter sequence. The promoter sequence is a strongly constitutive promoter sequence capable of driving a high level of expression of any polynucleotide sequence operably linked thereto. Another example of a suitable promoter is elongated growth factor-1a (EF-1α). However, other constitutive promoter sequences may also be used, including, but not limited to, the simian virus 40 (SV40) early promoter, mouse mammary tumor virus (MMTV), human immunodeficiency virus (HIV) long terminal repeat (LTR) promoter, MoMuLV promoter, the avian leukemia virus promoter, Epstein-Barr virus immediate early promoter, Rous sarcoma virus promoter, as well as human gene promoters such as, but not limited to the actin promoter, the myosin promoter, the hemoglobin promoter, and the creatine kinase promoter. Further, the present invention should not be limited to the use of constitutive promoters. Inducible promoters are also considered as part of the present invention. The use of an inducible promoter provides a molecular switch that can turn on the expression of a polynucleotide sequence which is operably linked to the inducible promoter when such expression is desired or turn off the expression when the expression is not desired. Examples of inducible promoters include but are not limited to a metallothionein promoter, a glucocorticoid promoter, a progesterone promoter, and a tetracycline promoter.

In order to evaluate the expression of the CAR polypeptide or part thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both of the selectable marker and reporter genes may be flanked with appropriate regulatory sequences to enable expression in host cells. Useful selectable markers include, for example, antibiotic resistance genes such as neo and the like.

Reporter genes are used to identify potentially transfected cells and to evaluate the functionality of regulatory sequences. Typically, the reporter gene is a gene that is not present in or expressed by the recipient organism or tissue and that encodes a polypeptide whose expression is clearly indicated by some readily detectable property such as enzyme activity. After DNA has been introduced into the recipient cells, the expression of the reporter gene is measured at an appropriate time. Suitable reporter genes may include genes encoding luciferase, β-galactosidase, chloramphenicol acetyltransferase, secretory alkaline phosphatase, or green fluorescent protein (e.g. Ui-Tei et al., 2000FEBS Letters 479: 79-82). Suitable expression systems are well known and may be prepared using known techniques or obtained commercially. Typically, the construct with at least 5 flanking regions showing the highest level of reporter gene expression is identified as the promoter. Such promoter region may be linked to a reporter gene and used to evaluate the ability of reagents to regulate promoter-driven transcription.

Methods of introducing and expressing genes into cells are known in the art. In the content of the expression vector, the vector may be readily introduced into a host cell, e.g., a mammalian, bacterial, yeast, or insect cell by any method in the art. For example, the expression vector can be transferred into a host cell by physical, chemical or biological means.

The physical methods for introducing a polynucleotide into a host cell include calcium phosphate precipitation, lipid transfection, particle bombardment, microinjection, electroporation and the like. Methods for producing cells comprising vectors and/or exogenous nucleic acids are well known in the art. See, for example, Sambrook et al. (2001, Molecular Cloning: A Laboratory Manual, Cold Spring Harbor Laboratory, New York). A preferred method for introducing a polynucleotides into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors may be derived from lentivirus, poxvirus, herpes simplex virus I, adenovirus and adeno-associated virus, etc. See, for example, U.S. Pat. Nos. 5,350,674 and 5,585,362.

Chemical means for introducing polynucleotides into host cells include colloidal dispersion systems, such as macromolecular complexes, nanocapsules, microspheres, beads, and lipid-based systems, including oil-in-water emulsions, micelles, mixed micelles and liposomes. An exemplary colloidal system used as a delivery vehicles in vitro and in vivo is a liposome (e.g., an artificial membrane vesicle).

In the case of using a non-viral delivery system, an exemplary delivery tool is a liposome. The use of lipid formulations is contemplated for the introduction of the nucleic acids into host cells (in vitro, ex vivo or in vivo). In another aspect, the nucleic acid may be associated with a lipid. The nucleic acid associated with a lipid may be encapsulated in the aqueous interior of a liposome, interspersed within the lipid bilayer of the liposome, attached to the liposome via a linker molecule associated with both the liposome and the oligonucleotide, entrapped in the liposome, complexed with the liposome, dispersed in solutions containing lipids, mixed with lipids, combined with lipids, contained in lipids as suspensions, contained or complexed with micelles, or otherwise associated with lipids. The lipid, lipid/DNA or lipid/expression vector associated with the composition is not limited to any specific structure in solution. For example, they may exist in bilayer structures, as micelles or have a "collapsed" structure. They may also be simply dispersed in solution, possibly forming aggregates of uneven size or shape. Lipids are fatty substances, which can be naturally occurring or synthesized lipids. For example, lipids include fatty droplets that occur naturally in the cytoplasm as well as the class of compounds which contain long-chain aliphatic hydrocarbons and their derivatives such as fatty acids, alcohols, amines, amino alcohols, and aldehydes.

In a preferred embodiment of the invention, the vector is a lentiviral vector.

Preparation

The present invention provides a preparation containing the CAR-T cell according to the first aspect of the present invention, and a pharmaceutically acceptable carrier, diluent or excipient. In one embodiment, the preparation is a liquid preparation. Preferably, the preparation is an injection. Preferably, the concentration of the CAR-T cells in the preparation is $1×10^3$-$1×10^8$ cells/ml, preferably $1×10^4$-$1×10^7$ cells/ml.

In one embodiment, the preparation may comprise buffers such as neutral buffered saline, sulfate buffered saline, and the like; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives. The preparation of the present invention is preferably formulated for intravenous administration.

Therapeutic Application

The present invention comprises therapeutic application using cells (e.g., T cells) transduced with lentiviral vectors (LV) encoding the expression cassette of the present invention. The transduced T cells can target tumor cell markers BCMA and/or CD19, and activate T cells synergistically to cause T cell immune response, thereby significantly improving its killing efficiency on tumor cells.

Thus, the present invention also provides a method for stimulating a T cell-mediated immune response to a target cell population or tissue in a mammal, comprising the step of administering the CAR-T cell of the invention to the mammal.

In one embodiment, the present invention comprises a type of cell therapy that autologous T cells from a patient (or heterologous donors) are isolated, activated and genetically modified to generate CAR-T cells, and then the CAR-T cells are injected into the same patient. In this way, the probability of graft-versus-host disease is extremely low, and antigens are recognized by T cells in a non-MHC-restricted manner. In addition, one kind of CAR-T can treat all cancers expressing this antigen. Unlike antibody therapy, CAR-T cells are able to replicate in vivo and result in long-term persistence that can lead to sustained tumor control.

In one embodiment, the CAR-T cells of the present invention can undergo stable in vivo T cell expansion and can persist for an extended amount of time. In addition, the CAR-mediated immune response may be part of an adoptive immunotherapy step in which CAR-modified T cells induce an immune response specific to the antigen-binding domain in the CAR. For example, anti-BCMA and/or CD19 CAR-T cells elicit a specific immune response against cells that express BCMA and/or CD19.

Although the data disclosed herein specifically discloses lentiviral vectors comprising anti-BCMA and/or CD19scFv, hinge and transmembrane domains, and 4-1BB/CD28 and CD3ξ signaling domains, the present invention should be construed to include any number of changes to each of the constituent parts of the construct.

Cancers that may be treated include tumors that are unvascularized or substantially unvascularized, as well as vascularized tumors. Cancers may include non-solid tumors (such as hematological tumors, for example, leukemia and lymphoma) or solid tumors. Types of cancers to be treated with the CAR of the present invention include, but are not limited to, carcinomas, blastocytomas and sarcomas, and certain leukemia or lymphoid malignancies, benign and malignant tumors, and malignant tumors, e.g., sarcomas, carcinomas and melanomas. Adult tumors/cancers and pediatric tumors/cancers are also included.

Hematological cancers are cancers of blood or bone marrow. Examples of hematological (or hematogenic) cancers include leukemia, including acute leukemia (such as acute lymphoblastic leukemia, acute myeloid leukemia, acute myelogenous leukemia and myeloblastic, promyelocytic, myelomonocytic, monocytic and erythroleukemia), chronic leukemia (such as chronic myelocytic (granulocytic) leukemia, chronic myelogenous leukemia and chronic lymphocytic leukemia), polycythemia vera, lymphoma, Hodgkin's disease, non-Hodgkin's lymphoma (painless and high-grade form), multiple myeloma, Waldenstrom's macroglobulinemia, heavy chain disease, myelodysplastic syndrome, hairy cell leukemia, and myelodysplasia.

Solid tumors are abnormal masses of tissue that usually do not contain cysts or liquid areas. Solid tumors can be benign or malignant. Different types of solid tumors are named after the cell types that form them (such as sarcoma, cancer and lymphoma). Examples of solid tumors such as sarcomas and cancers include fibrosarcoma, myxosarcoma, liposarcoma, mesothelioma, malignant lymphoma, pancreatic cancer, and ovarian cancer.

The CAR-modified T cells of the present invention may also be used as a type of vaccine for ex vivo immunization and/or in vivo therapy of mammals. Preferably, the mammal is a human.

For ex vivo immunization, at least one of the following occurs in vitro before the cell is administered into a mammal: i) expanding the cells, ii) introducing the nucleic acids encoding CAR into the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with vectors expressing the CAR disclosed herein. CAR-modified cells can be administered to a mammalian recipient to provide a therapeutic benefit. The mammalian recipient may be a human, and the CAR-modified cells may be autologous relative to the recipient. Alternatively, the cells may be allogeneic, syngeneic or xenogeneic with respect to the recipient.

In addition to using a cell-based vaccine for in vitro immunization, the present invention also provides compositions and methods for in vivo immunization to elicit an immune response against an antigen in a patient.

The present invention provides a method for treating a tumor comprising administering a therapeutically effective amount of CAR-modified T cells of the present invention to a subject in need thereof.

The CAR-modified T cells of the present invention may be administered alone or as a pharmaceutical composition in combination with diluents and/or with other components such as IL-2, IL-17 or other cytokines or cell populations. Briefly, the pharmaceutical compositions of the present invention may comprise a target cell population as described herein, in combination with one or more pharmaceutically or physiologically acceptable carriers, diluents, or excipients. Such compositions may comprise buffers such as neutral buffered saline, sulfate buffered saline, and the like; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives. The compositions of the present invention are preferably formulated for intravenous administration.

The pharmaceutical compositions of the present invention may be administered in a manner suitable for the disease to be treated (or prevented). The quantity and frequency of administration will be determined by factors such as the condition of the patient, and the type and severity of the patient's disease, although the appropriate dose may be determined by clinical trials.

When "an immunologically effective amount", "an anti-tumor effective amount", "a tumor-inhibitory effective amount" or "a therapeutic amount" is indicated, the precise amount of the composition of the invention to be administered may be determined by the physician, with consideration of individual differences in age, weight, tumor size, extent of infection or metastasis, and condition of the patient (subject). It may generally be stated that a pharmaceutical composition comprising the T cells described herein may be administered at a dosage of $10^4$ to $10^9$ cells/kg body weight, preferably $10^5$ to $10^6$ cells/kg body weight (including all integer values within those ranges). T cell compositions may also be administered multiple times at these dosages. Cells may be administered using infusion techniques that are well known in immunotherapy (see, for example, Rosenberg et al., New Eng. J. of Med. 319: 1676, 1988). The optimal dosage and treatment regimen for a particular patient can be easily determined by one skilled in the art of medicine by monitoring the patient for signs of disease and adjusting the treatment accordingly.

The administration of the subject composition may be performed in any convenient manner, including by spraying, injection, swallowing, infusion, implantation, or transplantation. The compositions described herein may be administered to a patient subcutaneously, intradermally, intratumorally, intramuscularly, intramuscularly, intravenously (i.v.) injection, or intraperitoneal. In one embodiment, the T cell composition of the present invention is administered to a patient by intradermal or subcutaneous injection. In another embodiment, the T cell composition of the present invention is preferably administered by i.v. injection. The composition of T cells may be directly injected into tumors, lymph nodes or infected sites.

In certain embodiments of the present invention, cells that are activated and expanded using the methods described herein or other methods known in the art for extending T cells to therapeutic levels are administered to a patient in conjunction with (e.g., before, simultaneously or subsequently) any number of related treatment forms, including but not limited to treatment with agents such as antiviral therapy, cidofovir and interleukin-2, cytarabine (also known as ARA-C) or natalizumab treatment for MS patients or efalizumab treatment for psoriasis patients or other treatments for PML patients. In further embodiments, the T cells of the present invention may be used in combination with chemotherapy, radiation, immunosuppressants such as cyclosporine, azathioprine, methotrexate, mycophenolate and FK506, antibodies or other immunotherapeutic agents. In a further embodiment, the cell composition of the present invention is administered to a patient in combination with (e.g. before, simultaneously, or subsequently) bone marrow transplantation, or the use of chemotherapy agents such as fludarabine, external-beam radiotherapy (XRT), cyclophosphamide. For example, in one embodiment, the subject may undergo standard treatment of high-dose chemotherapy followed by peripheral blood stem cell transplantation. In some embodiments, after transplantation, the subject receives an injection of extended immune cells of the present invention. In an additional embodiment, the expanded cells are administered before or after surgery.

The dosage of the above treatments to be administered to the patient will vary with the precise nature of the condition being treated and the recipient of the treatment. The scaling of dosage for human administration can be implemented according to accepted practices in the art. In general, for each treatment or course of treatment, $1 \times 10^6$ to $1 \times 10^{10}$ of the modified T cells of the present invention (e.g. CAR-T cells) can be administered to patients by means of, e.g. intravenous reinfusion.

The Main Advantages of the Invention Include:

(a) The constructed CAR-T cells containing J scFv of the present invention have higher tumor killing and functional activities in vivo and in vitro than BB and April CAR-T.

(b) The constructed bispecific CAR-T of the present invention can simultaneously recognize two or more targets including BCMA.

The present invention will be further illustrated below with reference to the specific examples. It is to be understood that these examples are for illustrative purposes only and are not intended to limit the scope of the invention. The experimental methods without detailed conditions in the following examples are generally in accordance with conventional conditions, or in accordance with the conditions recommended by the manufacturer. Unless otherwise stated, percentages and parts are calculated by weight.

Example 1 Isolation of PBMC and Amplification of T Cells from Donor Blood

Mononuclear cells were isolated from donor blood, and centrifuged with density gradient using Histopaque-1077 (Sigma-Aldrich). The T cells were enriched (EasySep Human T Cell Enrichment Kit, Stemcell Technologies). The T cells were activated, cultured and amplified using magnetic beads coupled with anti-CD3/anti-CD28. X-vivo15 (300 IU/ml rhIL2) was used as culture medium. All cells were cultured in a constant temperature incubator at 37° C., 5% $CO_2$.

Example 2 Cell Culture and Construction

BCMA-expressing cell lines MM.1s and RPMI8226, MM.1s-ffluc cells, RPMI8226-ffluc cells, Hela cells expressing BCMA, CD19 and BCMA/CD19 at the same time, the above cells were cultured in RPMI 1640 medium; 293T (human renal epithelial cell line, ATCC® CRL-3216) was cultured using DMEM medium. All medium were supplemented with 10% (v/v) fetal bovine serum, 100 U/ml penicillin and streptomycin, 2 mM L-glutamine and 1 mM sodium pyruvate.

Among them, Hela cells expressing BCMA, CD19 and BCMA/CD19 at the same time were stable cell lines obtained by transferring BCMA and CD19 antigens through lentiviral vectors, which can specifically express BCMA or/and CD19 protein molecules. MM.1s-ffluc cells and RPMI8226-ffluc cells are stable cell lines screened after lentivirus infection with firefly luciferase.

Example 3 CAR Structural Design and Transduction

A single CAR targeting BCMA and a dual CAR targeting BCMA and CD19 were designed and constructed. The structure is schematically shown in FIG. 1. Specifically, the CAR structure of the present invention is shown in FIG. 1, and the designation and composition are shown in Table 1.

TABLE 1

| Structure of CAR | | |
|---|---|---|
| Structure naming | Structure composition | CAR-T Name |
| J1 | SingleJ scFv | CAR-J1 |
| J2 | Parallel CD19 CAR + J1 CAR (Dual CAR) | CAR-J2 |
| J3 | Parallel J1 CAR + CD19 CAR (Dual CAR) | CAR-J3 |
| J4 | CAR of CD19 scFv + J scFv with loop structure | CAR-J4 |
| S5 | Serial J scFv + CD19 scFv CAR | CAR-S5 |
| BB | Single BB scFv | CAR-BB |
| April | Single April chain | CAR-April |
| 19-BB | Parallel CD19 CAR + BB CAR (Dual CAR) | CAR-19-BB |
| 19 | SingleCD19 scFv | CAR-19 |

The specific sequences of elements involved in the CAR described in FIG. 1 and Table 1 are as follows:

```
J scFv heavy chain
                                    (SEQ ID NO: 9)
QVQLQQSGGGLVQPGGSLKLSCAASGIDFSRYWMSWVRRAPGKGLEWIGE

INPDSSTINYAPSLKDKFIISRDNAKNTLYLQMSKVRSEDTALYYCASLY

YDYGDAMDYWGQGTSVTVSS

J scFv light chain
                                    (SEQ ID NO: 10)
DIVMTQSQRFMTTSVGDRVSVTCKASQSVDSNVAWYQQKPRQSPKALIFS

ASLRFSGVPARFTGSGSGTDFTLTISNLQSEDLAEYFCQQYNNYPLTFGA

GTKLELK

BB scFv heavy chain
                                    (SEQ ID NO: 13)
DIVLTQSPPSLAMSLGKRATISCRASESVTILGSHLIHWYQQKPGQPPTL

LIQLASNVQTGVPARFSGSGSRTDFTLTIDPVEEDDVAVYYCLQSRTIPR

TFGGGTKLEIK

BB scFv light chain
                                    (SEQ ID NO: 14)
QIQLVQSGPELKKPGETVKISCKASGYTFTDYSINWVKRAPGKGLKWMGW

INTETREPAYAYDFRGRFAFSLETSASTAYLQINNLKYEDTATYFCALDY

SYAMDYWGQGTSVTVSSAAA

April chain
                                    (SEQ ID NO: 15)
SVLHLVPINATSKDDSDVTEVMWQPALRRGRGLQAQGYGVRIQDAGVYLL

YSQVLFQDVTFTMGQVVSREGQGRQETLFRCIRSMPSHPDRAYNSCYSAG

VFHLHQGDILSVIIPRARAKLNLSPHGTFLGFVKLSGGGSDP
```

-continued

CD8 signal peptide
(SEQ ID NO: 16)
MALPVTALLLPLALLLHAARP (G4S)3 linker peptide
(SEQ ID NO: 17)
GGGGSGGGGSGGGGS (G4S)5 linker peptide
(SEQ ID NO: 18)
GGGGSGGGGSGGGGSGGGGSGGGGS 218 linker peptide
(SEQ ID NO: 19)
GSTSGSGKPGSGEGSTKG CD8 hinge region
(SEQ ID NO: 8)
TTTPAPRPPTPAPTIASQPLSLRPEACRPAAGGAVHTRGLDFACD (SEQ ID NO: 21)
OrKPTTTPAPRPPTPAPTIASQPLSLRPEASRPAAGGAVHTRGLDFASDK

P or (SEQ ID NO: 22)
SGTTTPAPRPPTPAPTIASQPLSLRPEACRPAAGGAVHTRGLDFACD

CD8 transmembrane region
(SEQ ID NO: 7)
IYIWAPLAGTCGVLLLSLVITLYC

CD28 transmembrane region
(SEQ ID NO: 6)
FWVLVVVGGVLACYSLLVTVAFIIFWV

41BB signal region
(SEQ ID NO: 5)
KRGRKKLLYIFKQPFMRPVQTTQEEDGCSCRFPEEEEGGCEL

CD28 signal region
(SEQ ID NO: 4)
RSKRSRLLHSDYMNMTPRRPGPTRKHYQPYAPPRDFAAYRS

CD3z signal region
(SEQ ID NO: 3)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR (SEQ ID NO: 23)
orRVKFSRSADAPAYQQGQNQLYNELNLGRREEYDVLDKRRGRDPEMGGK

PQRRKNPQEGLYNELQKDKMAEAYSEIGMKGERRRGKGHDGLYQGLSTAT

KDTYDALHMQALPPR 2A peptide
(SEQ ID NO: 2)
GSGATNFSLLKQAGDVEENP

FMC63 scFv (CD19 scFv) heavy chain
(SEQ ID NO: 11)
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

FMC63 scFv (CD19 scFv) light chain
(SEQ ID NO: 12)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT

-continued

GM-CSF signal peptide
(SEQ ID NO: 1)
MLLLVTSLLLCELPHPAFLLIP

EGFRt sequence
(SEQ ID NO: 20)
RKVCNGIGIGEFKDSLSINATNIKHFKNCTSISGDLHILPVAFRGDSFTH

TPPLDPQELDILKTVKEITGFLLIQAWPENRTDLHAFENLEIIRGRTKQH

GQFSLAVVSLNITSLGLRSLKEISDGDVIISGNKNLCYANTINWKKLFGT

SGQKTKIISNRGENSCKATGQVCHALCSPEGCWGPEPRDCVSCRNVSRGR

ECVDKCNLLEGEPREFVENSECIQCHPECLPQAMNITCTGRGPDNCIQCA

HYIDGPHCVKTCPAGVMGENNTLVWKYADAGHVCHLCHPNCTYGCTGPGL

EGCPTNGPKIPSIATGMVGALLLLLVVALGIGLFM

The CAR genes in Table 1 were cloned into the skeleton of FUW lentivirus vector to construct a complete lentivirus expression vector which can be used to infect T cells. Specifically, taking the BCMA CAR gene as an example, the BCMA CAR gene was placed under the promoter of EF1α (EF-1α) to form Fuw-EF1α-BCMA CAR, and three plasmids including Fuw-EF1a-BCMA CAR, lentiviral envelope plasmid pMD2.G (Addgene, Plasmid #12259) and lentiviral packaging plasmid psPAX2 (Addgene, Plasmid #12260) were transferred into 293T using Lipofectamine3000 to prepare lentiviral complete expression vector. The virus supernatant was collected at 48 h and 72 h, and concentrated by ultracentrifugation. The concentrated virus could be used to infect T cells.

The results of flow cytometry analysis show that the constructed CAR gene can be used to produce lentiviral vector expressing BCMA CAR.

Example 4 Preparation of CAR-T Cell

The experimental methods were as follows:

4.1 Lentivirus Infection

After activation for 2 days, the isolated and purified primary T cells were infected with lentiviral vectors constructed in Example 3, transferred to a cell culture flask, and cultured in a constant temperature incubator at 37° C., 5% $CO_2$.

4.2 Detection of Cell Proliferation and CAR Positive Rate

After the 3rd day of infection and before cryopreservation, BCMA antigen was used to detect the number of cells and the proportion of BCMA positive cells, that is, to detect the CAR positive rate of T cells, and half of the culture medium was changed every 2-3 days.

The results show that CAR-T cells are successfully produced using the lentiviral vectors packaged in Example 3, and the names are shown in Table 1.

Specifically, the construction results of BCMA CAR-T cells are shown in FIG. 2. The expression of BCMA CAR can be detected in CAR-BB and CAR-J1 CAR-T cells after virus transduction, and the expression of CAR can reach more than 50%.

Example 5 Cell Killing In Vitro

CAR-J1 CAR-T cells, CAR-BB CAR-T cells and CAR-April CAR-T cells obtained in Example 4 were subjected to in vitro killing assay. The killing of CAR-T cells to Hela cell lines over-expressing BCMA was tested by RTCA assay.

Figure 3:
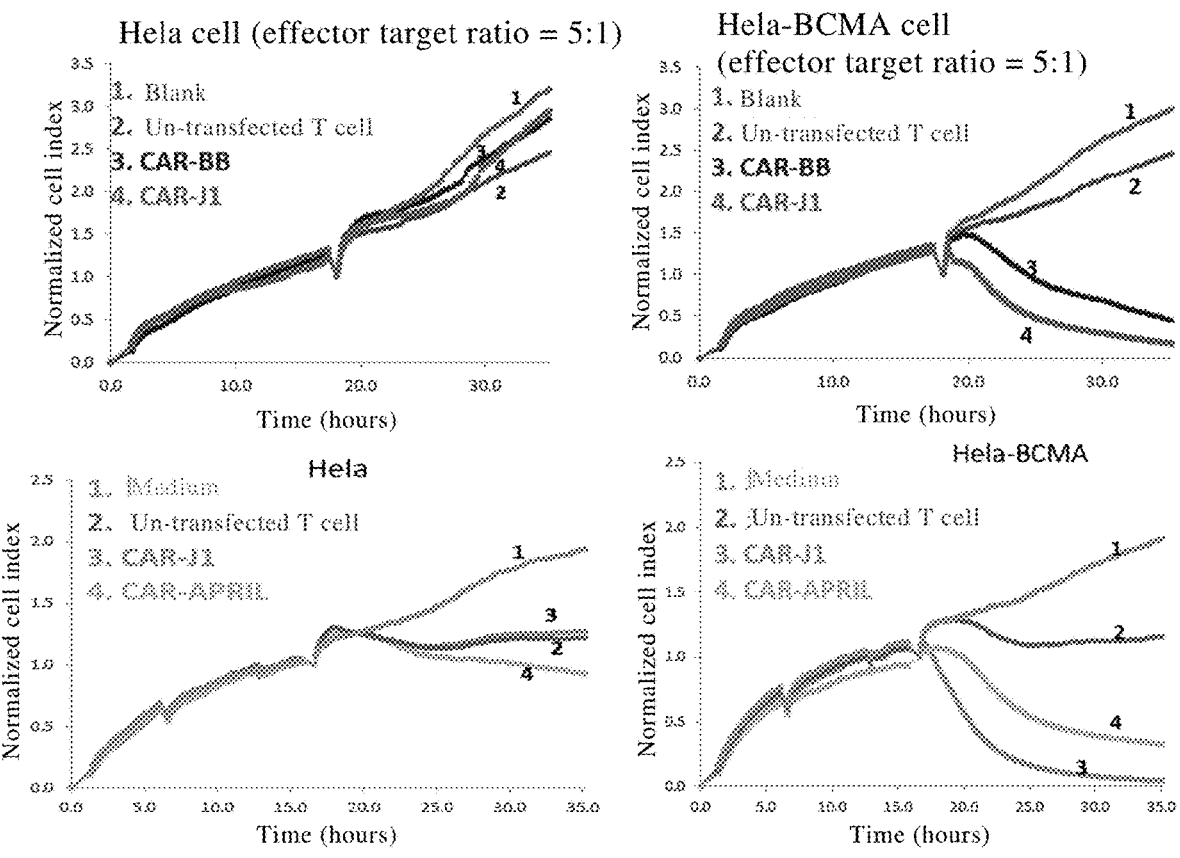
FIG. 3 shows the killing results of CAR-BB and CAR-J1 on Hela cells and over-expressed BCMA cells (Hela-BCMA) respectively (RTCA method), and the killing results of CAR-April and CAR-J1 on Hela cells and over-expressed BCMA cells (Hela-BCMA) respectively (RTCA method) in the present invention.

The results are as shown in FIG. 3 (RTCA test). NT control group (untransfected T cell control group) and culture medium control group (blank control group) do not kill Hela-BCMA cells, while CAR-J1 cells can exert BCMA-specific killing function, and CAR-J1 cells are superior to CAR-BB cells in killing BCMA-positive Hela-BCMA cells.

Then, the killing ability of tumor target cells labeled with luciferase was detected. The luciferase gene was transferred into target cells, and MM.1s-Luc and RPMI8226-Luc stable cell lines were obtained after cloning and screening. In the experiment, when luciferin substrate was added, luciferase reacted with luciferin to produce fluorescence. By detecting the intensity of fluorescence, the activity of luciferase and the survival rate of cells could be measured, and the killing effect of CAR-T cells could be obtained.

Figure 4:
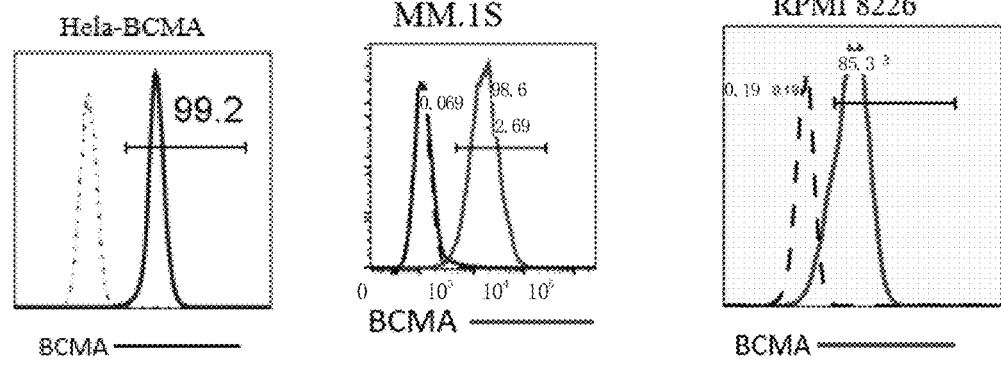
FIG. 4 shows the BCMA expression of the target cells used in the present invention.
Figure 5:
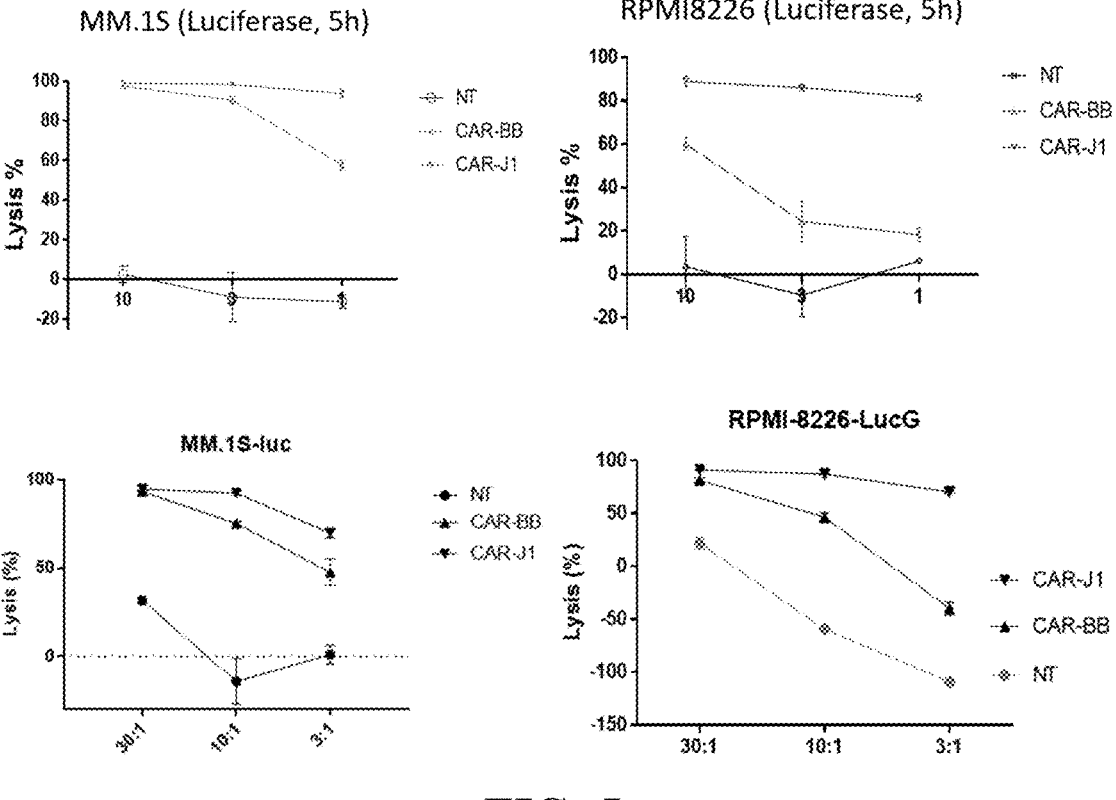
FIG. 5 shows the results of in vitro killing experiments of different batches of CAR-BB and CAR-J1 on MM.1s cells and RPMI-8226 cells, respectively (Luciferase method).

FIG. 4 shows the antigen expression on the target cell surface. FIG. 5 shows that under the same E:T ratio, NT cells have no killing function, while CAR-J1 cells have dose-dependent killing effect on MM.1S-Luc cells (MM.1S cells with luciferase gene) and RPMI8226-Luc cells (RPMI8226 cells with luciferase gene), and CAR-J1 cells have better killing ability than CAR-BB and CAR-April.

In addition, the applicant also constructed CAR-T cells using a variety of common targeting BCMA scFv in the art. After testing, these CAR-T cells do not show ideal killing function.

In summary, after CAR-T cells were co-cultured with target cells (BCMA overexpressing cells, BCMA-positive tumor cells, MM.1s-Luc and RPMI8226 cells), the target cells could be lysed by CAR-T cells targeting BCMA, and CAR-J1 showed higher killing ability than CAR-BB. Other CAR-T cells constructed by scFv targeting BCMA that are common in the art, do not show ideal killing function.

Example 6 Cytokine Release Assay

The CAR T cells targeting BCMA (CAR-J1 CAR T cells and CAR-BB CAR T cells) obtained in Example 4 were mixed with tumor cells (Hela, Hela-BCMA, Hela-CD19, Hela-BCMA-CD19) and placed in RPMI medium at a density of $1\times10^4$/ml of each cell. 100 ul of CAR-T cells and 100 ul of tumor cells were cultured overnight in 96-well plates. The supernatant was collected and centrifuged to detect the release level of cytokines such as IFN-γ. Elisa kit was used for detection.

Figure 6:
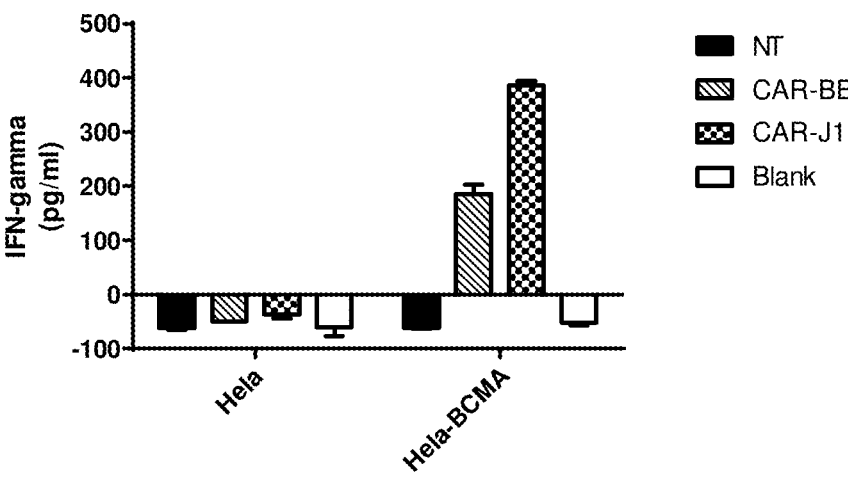
FIG. 6 shows the release of IFNr cytokines during the killing of Hela cells and over-expressed BCMA cells (Hela-BCMA) by CAR-BB and CAR-J1 respectively in the present invention.

The results are as shown in FIG. 6. After CAR-J1 is co-stimulated by Hela-BCMA target cells, the secretion of cytokine INF-γ is significantly higher than that of CAR-BB, but there is no obvious secretion in NT and Medium groups.

Example 7 In Vivo Pharmacodynamic Study

NOG mice aged 6-12 weeks were selected and injected subcutaneously with $1\times10^7$ RPMI8226 cells. Two days later, the load of tumor grafts was measured. After 10 days, mice were divided into groups. CAR-J1 CAR-T cells and CAR-BB CAR-T cells were injected one day after grouping, respectively. After CAR-T treatment, the tumor volume load of mice was evaluated twice a week.

Figure 7:
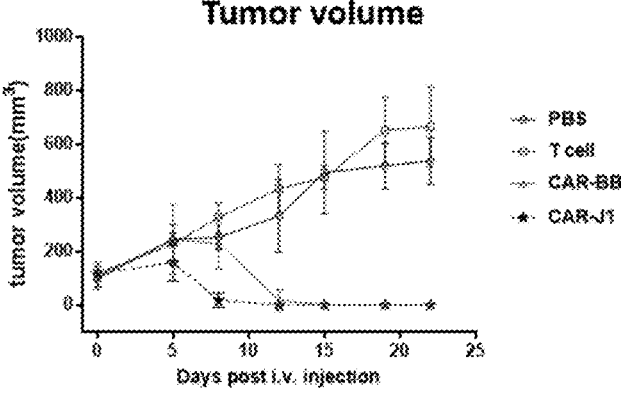
FIG. 7 shows the tumor elimination ability of CAR-BB and CAR-J1 after intravenous infusion of the immunodeficient mouse RPMI-8226 subcutaneous model model in the present invention.

The results are as shown in FIG. 7. Compared with the control group, the ability of eliminating tumor burden in mice injected with CAR-J1 cells is significantly higher than that in CAR-BB group, and there is no significant change in body weight.

Example 8 Preparation of Dual CAR-T Cells

The experimental methods were as follows:

In this example, CAR-T cells targeting both BCMA and CD19 are involved, and the structure of CAR is schematically shown in FIG. 1 (CAR J2, CAR J3, CAR J4). The scFv in the BCMA CAR structure is composed of the scFv heavy chain and the light chain of J and BB, wherein the J scFv is composed of SEQ ID NO: 9 and SEQ ID NO: 10; BB scFv is composed of SEQ ID NO: 13 and SEQ ID NO: 14; CD19 scFv is composed of SEQ ID NO: 11 and SEQ ID NO: 12; In addition, scFv can be replaced by the BCMA binding region composed of the April partial sequence (SEQ ID NO: 15) to form a new CAR structure.

The BCMA-CD19 CAR gene was cloned into the vector skeleton and placed under the promoter of EF1 α (EF-1 α). The lentiviral complete expression vector was prepared by transferring EF1 α-BCMA-CD19 CAR plasmid and lentiviral envelope plasmid into 293T using Lipofectamine3000. The virus supernatant was collected at 48 h and 72 h, and then concentrated by ultracentrifugation. The concentrated virus could be used to infect T cells.

Lentivirus infection: After activation for 2 days, the isolated and purified primary T cells were infected with lentiviral vectors constructed above at MOI (1-10), transferred to a cell culture flask, and cultured in a constant temperature incubator at 37° C., 5% $CO_2$.

Detection of cell proliferation and CAR positive rate: The number of cells and the proportion of BCMA/CD19 dual positive cells were detected on the 3rd day after infection and before cryopreservation, that is, to detect the CAR positive rate of T cells, and half of the culture medium was changed every 2-3 days.

The results show that BCMA-CD19 CAR-T cells are successfully constructed by using the BCMA-CD19 CAR lentiviral vector, as shown in FIG. 1 and Table 1.

Figure 8:
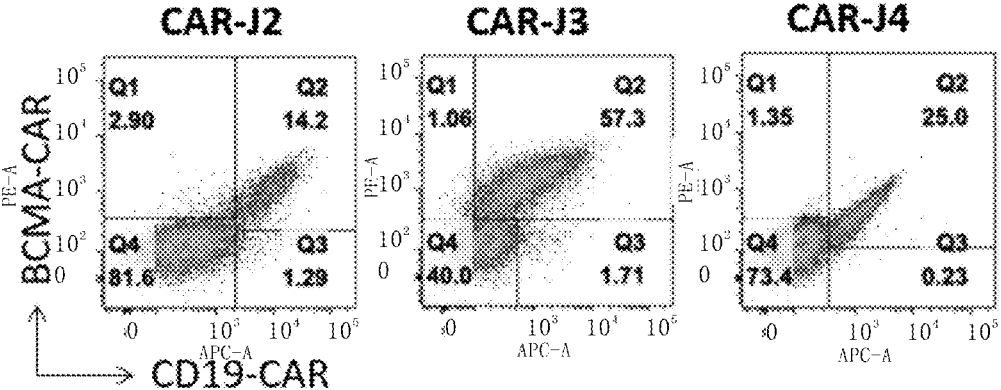
FIG. 8 shows the expression of CD19-CAR and BCMA-CAR in bispecific CAR-T cells of the present invention.

The results are as shown in FIG. 8. The expression of BCMA CAR and CD19 CAR can be detected on the surface of T cells after virus transfection using BCMA antigen and CD19 antigen.

Example 9 Cell Killing In Vitro

The CAR-T cells obtained in Example 8 were subjected to in vitro killing assay. The overexpressing Hela cell lines that overexpressed BCMA and CD19 were used for RTCA or luciferase-labeled tumor target cells were used for detection. The luciferase gene was transferred into target cells, and stable cell lines (RPMI8226, MM.1s and Nalm6) were obtained after cloning and screening. In the experiment, when luciferin substrate was added, luciferase reacted with luciferin to produce fluorescence. By detecting the intensity of fluorescence, the activity of luciferase and the survival rate of cells could be measured, and the killing effect of CART cells could be obtained.

The results show that all the target cells (CD19/BCMA dual positive, CD19 single positive, BCMA single positive) were lysed after CAR-T cells and the target cells above were co-cultured, which indicates that BCMA-CD19 CAR-T has killing effect on CD19/BCMA dual positive, CD19 single positive and BCMA single positive cells.

Figure 9:
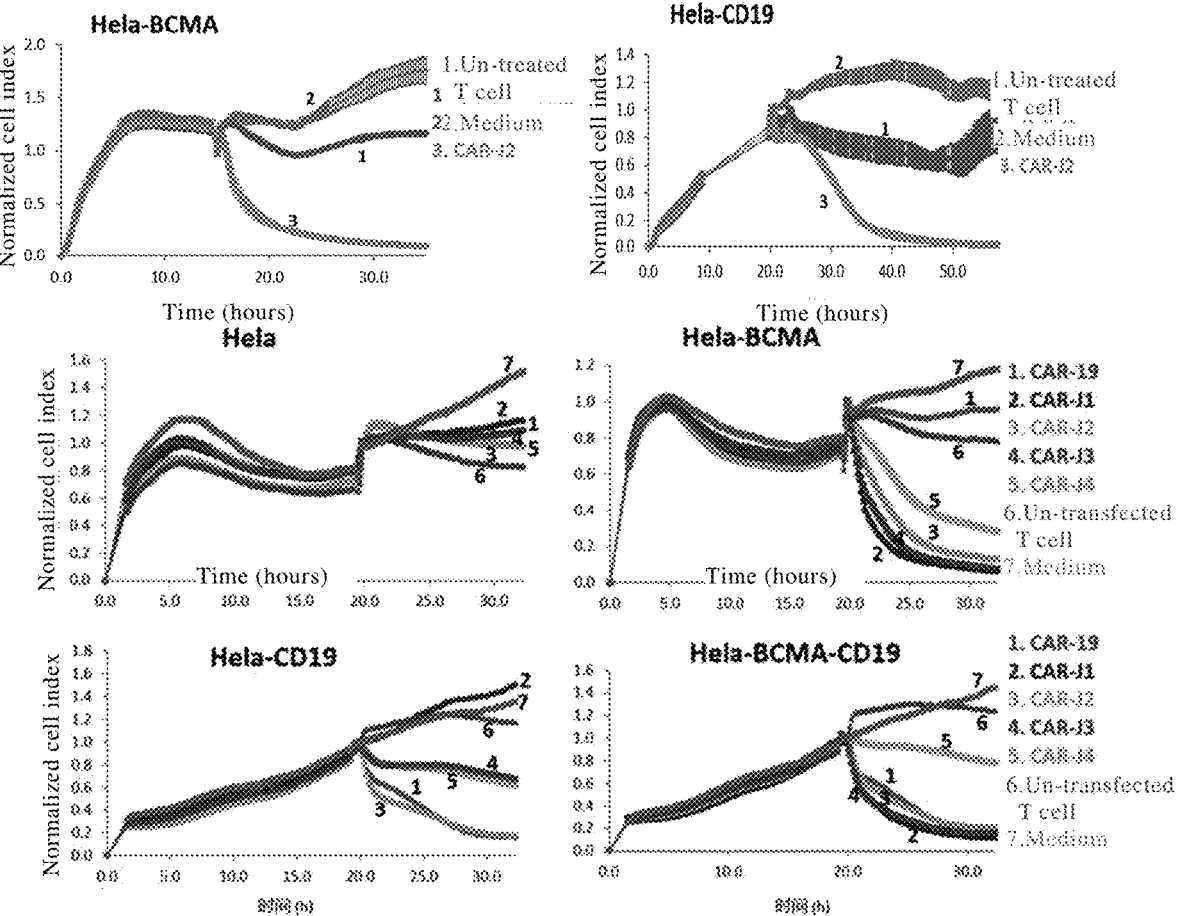
FIG. 9 shows a comparison of the killing of Hela and Hela overexpression antigen cell lines Hela-BCMA, Hela-CD19 and Hela-BCMA-CD19 by different batches of bispecific CAR-T, CAR-19 and CAR-BCMA in the present invention.

The results are as shown in FIG. 9. The bispecific CAR-T can significantly kill both single positive CD19 positive target cells (Hela-CD19) and single positive BCMA positive target cells (Hela-BCMA), and also significantly kill both CD19 and BCMA positive target cells Hela-BCMA CD19, indicating that BCMA and CD19 combined bispecific CAR-T cells can kill both single-target and dual-target cells. However, single CAR-T (CAR-19 or CAR-J1) can only kill one target antigen.

Figure 10:
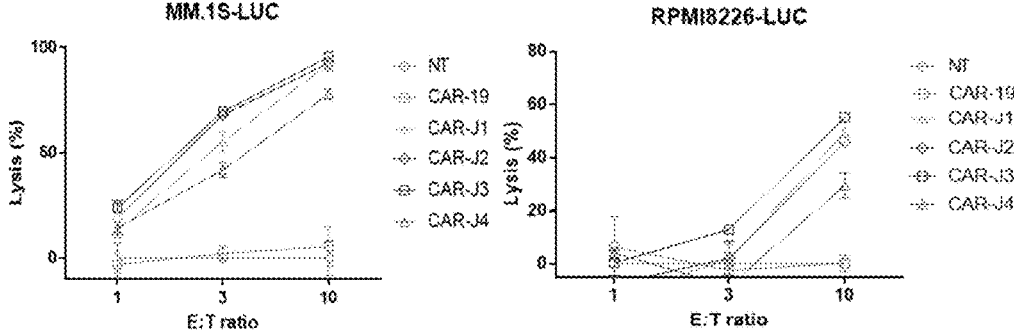
FIG. 10 shows the results of in vitro killing experiments (Luciferase method) of MM.1s cells, RPMI-8226 cells and Nalm6 cells by different batches of CAR-CD19, CAR-BCMA and bispecific CAR-T in the present invention.

FIG. 10 shows that dual CAR-T can significantly kill BCMA single-positive tumor target cells MM.1s and RPMI8226. And it can significantly kill the CD19 single-positive tumor target cell Nalm6. It indicates that the dual CAR combined with BCMA and CD19 has a killing effect on BCMA and CD19 positive tumor target cells.

Example 10 Up-Regulation of CD107 after Stimulation

The CAR-T cells obtained in Example 8 were subjected to flow cytometry analysis of CD107a expression changes after activation, and a co-incubation activation experiment was performed using tumor cell lines expressing CD19 or BCMA. The cells after co-incubation were labeled with antibodies for CD3, CD8, and CD107a, and then flow cytometric analysis was performed.

Figure 11:
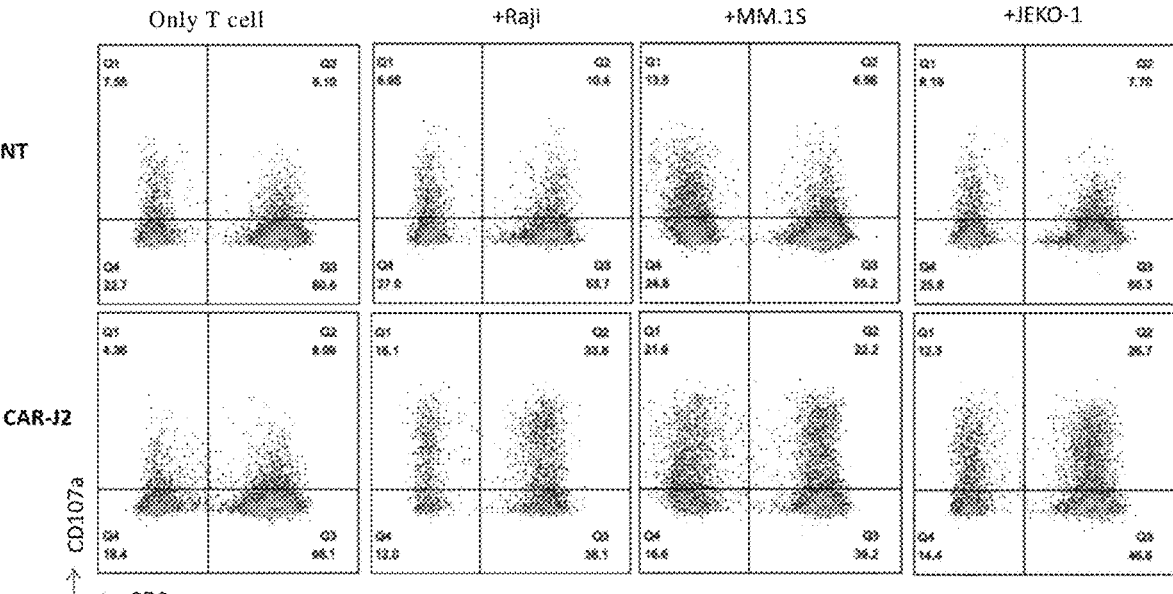
FIG. 11 shows analysis of CD107a expression on the surface after dual CAR-T cells co-cultured with MM.1s, Raji and Jeko-1 tumor target cells.

The results are as shown in FIG. 11. The CD107a molecule on the surface of CAR-T cells is significantly up-regulated after co-culture of dual CAR-T cells of BCMA-positive tumor target cells MM.1s, CD19-positive Raji and dual-positive Jeko-1 tumor target cells.

Example 11 In Vivo Pharmacodynamic Study

NOG mice aged 6-12 weeks were selected and injected intravenously with $1 \times 10^7$ MM.1s cells. Two days later, the tumor graft load was measured. And 10 days later, the mice were divided into groups, and CAR-T cells were injected with high and low doses one day after grouping. After CAR-T treatment, the tumor burden of mice was evaluated twice a week. Each mouse was intraperitoneally injected with 3 mg d-luciferin (Perkin Elmer Life Sciences), and photographed with Xenogen IVIS Imaging System (Perkin Elmer Life Sciences) four minutes later, and exposed for 30s. The signal of bioluminescence is calculated according to the amount of photons emitted, and the amount of photons is normalized by exposure time and surface area, and finally the amount of photons/s/cm$^2$/steradian (p/s/cm$^2$/sr) is obtained.

Figure 12:
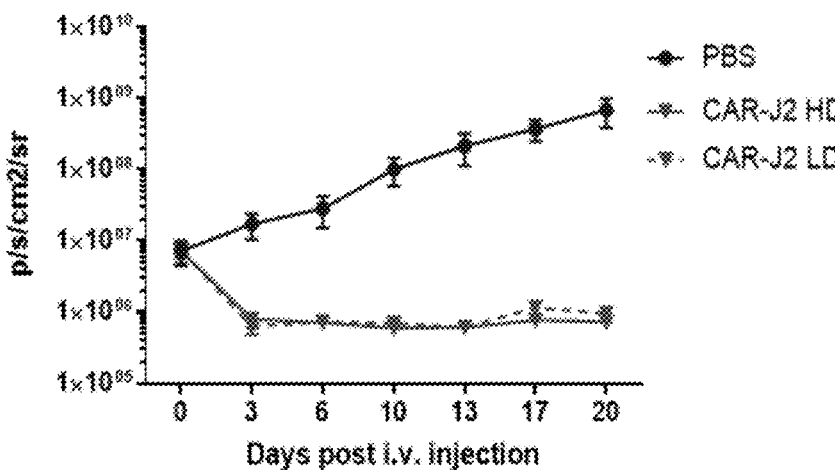
FIG. 12 shows the tumor elimination ability after intravenous reinfusion of different doses of bispecific CAR-J2 cells to the immunodeficient mouse MM.1s-luc intravenous modeling model.

The results of FIG. 12 show that compared with the control group, the tumor burden of mice injected with dual CAR-T cells decreased significantly until disappeared, indicating that BCMA-CD19 CAR-T cells have significant anti-tumor effect.

Example 12

The killing ability was detected by using Raji lymphoma target cells labeled with luciferase. The luciferase gene was transferred into Raji target cells, and the stable cell line Raji-Luc was obtained after cloning and screening. In the experiment, when luciferin substrate was added, luciferase reacted with luciferin to produce fluorescence. By detecting the intensity of fluorescence, the activity of luciferase and the survival rate of cells could be measured, and the killing effect of CAR-T cells could be obtained.

Figure 13:
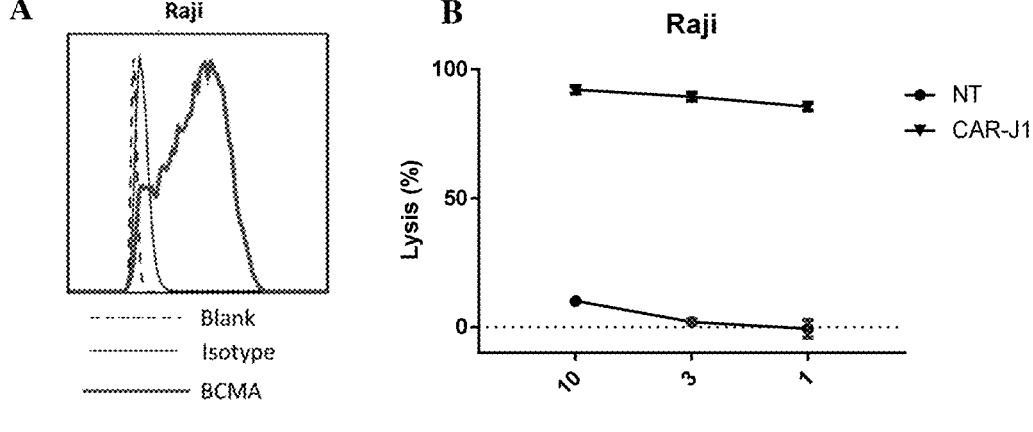
FIG. 13 shows the results of in vitro killing experiments of CAR-J1 on Raji lymphoma cells (Luciferase method). Among them.

The results are as shown in FIG. 13. NT cells do not have killing function, and CAR-J1 cells have a dose-dependent killing effect on Raji-Luc cells (Raji cells transferred with luciferase gene), indicating its potential application value for lymphoma indications.

All literatures mentioned in the present application are incorporated by reference herein, as though each one is individually incorporated by reference. In addition, it should be understood that after reading the above teaching content of the present invention, various changes or modifications may be made by those skilled in the art, and these equivalents also fall within the scope as defined by the appended claims of the present application.

The invention claimed is:

1. A bispecific chimeric antigen receptor (CAR), comprising:

a first CAR targeting CD19; and a second CAR targeting B-Cell maturation antigen (BCMA); wherein the first CAR and the second CAR are linked by a 2A peptide, wherein the structure of the first CAR is shown in Formula V:

$$L\text{-}scFv1'\text{-}H\text{-}TM\text{-}C\text{-}CD3\zeta \qquad (V)$$

wherein the structure of the second CAR is shown in Formula (I):

$$L\text{-}scFv\text{-}H\text{-}TM\text{-}C\text{-}CD3\zeta \qquad (I)$$

wherein, each "-" is independently a linker peptide or a peptide bond;

L is none or a signal peptide sequence;

H is none or a hinge region;

TM is a transmembrane domain;

C is a co-stimulatory signal molecule;

CD3$\zeta$ is a cytoplasmic signal transduction sequence derived from CD3$\zeta$;

scFv1' is an antigen binding domain targeting CD19BCMA, comprising an antibody heavy chain variable region shown in SEQ ID NO: 11 and an antibody light chain variable region shown in SEQ ID NO: 12;

the structure of the antigen binding domain targeting CD19 is shown in Formula (C):

$$V_{L1}\text{-}V_{H1} \qquad (C)$$

wherein $V_{H1}$ is the antibody heavy chain variable region $V_{L1}$ is the antibody light chain variable; and "-" is a linker peptide or a peptide bond;

scFv is an antigen binding domain targeting BCMA, comprising an antibody heavy chain variable region shown in SEQ ID NO: 9 and an antibody light chain variable region shown in SEQ ID NO: 10;

the structure of the antigen binding domain targeting BCMA is shown in Formula (A):

$$V_H\text{-}V_L \qquad (A)$$

wherein $V_H$ is the antibody heavy chain variable region;

$V_L$ is the antibody light chain variable; and

"-" is a linker peptide or a peptide bond.

2. A method for enhancing viability of immune cells in vivo or killing ability of immune cells to tumor cells with clonal proliferation ability, comprising expressing the bispecific CAR of claim 1 in the immune cells.

3. The bispecific CAR of claim 1, wherein the L is a signal peptide of a protein selected from the group consisting of: a CD8, CD28, GM-CSF, CD4, CD137, or a combination thereof.

4. The bispecific CAR of claim 3, wherein the L comprises a CD8 signal peptide.

5. The bispecific CAR of claim 1, wherein the H comprises a hinge region from CD8, CD28, CD137, or a combination thereof.

6. The bispecific CAR of claim 5, wherein at least one H comprises a hinge region from CD8.

7. The bispecific CAR of claim 1, wherein the TM comprises a transmembrane region of CD28, CD3 epsilon, CD45, CD4, CD5, CD8, CD9, CD16, CD22, CD33, CD37, CD64, CD80, CD86, CD134, 4-1BB (CD137), CD154, or a combination thereof.

8. The bispecific CAR of claim 7, wherein each TM independently comprises a CD8 or CD28 transmembrane region.

9. The bispecific CAR of claim 1, wherein the C comprises a co-stimulatory signal molecule of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, or a combination thereof.

10. The bispecific CAR of claim 9, wherein each C independently comprises a CD28 and/or 4-1BB co-stimulatory signal molecule.

11. The bispecific CAR of claim 1, wherein the CD32 comprises the amino acid of SEQ ID NO: 3.

12. A nucleic acid molecule encoding the bispecific CAR of claim 1.

13. A vector comprising the nucleic acid molecule of claim 12.

14. An engineered immune cell comprising an exogenous nucleic acid molecule of claim 12.

15. An engineered immune cell comprising the vector of claim 13.

16. A method for enhancing viability of immune cells in vivo or killing ability of immune cells to tumor cells with clonal proliferation ability, comprising expressing the bispecific CAR of claim 6 in the immune cells.

* * * * *